United States Patent
Colloca et al.

(10) Patent No.: US 10,588,961 B2
(45) Date of Patent: Mar. 17, 2020

(54) POXVIRAL VACCINES

(71) Applicant: GLAXOSMITHLKINE BIOLOGICALS, SA, Rixensart (BE)

(72) Inventors: Stefano Colloca, Rome (IT); Riccardo Cortese, Basel (CH); Antonella Folgori, Rome (IT); Alfredo Nicosia, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/848,100

(22) Filed: Dec. 20, 2017

(65) Prior Publication Data

US 2018/0125968 A1    May 10, 2018

Related U.S. Application Data

(62) Division of application No. 14/770,510, filed as application No. PCT/IB2014/059802 on Mar. 14, 2014, now abandoned.

(30) Foreign Application Priority Data

Mar. 15, 2013 (WO) .................. PCT/EP2013/055409

(51) Int. Cl.
| | |
|---|---|
| *A61K 39/275* | (2006.01) |
| *A61K 39/235* | (2006.01) |
| *C07K 14/065* | (2006.01) |
| *C07K 14/075* | (2006.01) |
| *A61K 39/29* | (2006.01) |
| *A61K 39/00* | (2006.01) |
| *C07K 14/74* | (2006.01) |
| *C07K 14/005* | (2006.01) |
| *C12N 7/00* | (2006.01) |
| *C12N 15/86* | (2006.01) |

(52) U.S. Cl.
CPC .............. *A61K 39/29* (2013.01); *A61K 39/00* (2013.01); *C07K 14/005* (2013.01); *C07K 14/70539* (2013.01); *C12N 7/00* (2013.01); *C12N 15/86* (2013.01); *A61K 2039/53* (2013.01); *C07K 2319/00* (2013.01); *C12N 2710/24041* (2013.01); *C12N 2710/24143* (2013.01); *C12N 2770/24222* (2013.01); *C12N 2770/24234* (2013.01)

(58) Field of Classification Search
CPC .. A61K 2039/5254; C12N 2760/12234; C12N 2760/18722; C12N 2770/24143; C12N 2800/22; C12N 2830/00; C12N 2501/50; C12N 15/86; C12N 15/64; C12N 15/85; C12N 2710/10043; C12N 2710/10343; C12N 2710/16143; C07K 14/005; C07K 14/175; C07K 16/2833; C07K 14/70539; C07K 2319/00; C07K 14/52; C07K 16/24; C07K 14/705; C07K 16/28; C07K 16/2803; C07K 16/3061; C07K 16/468; G01N 2333/175

See application file for complete search history.

(56) References Cited

U.S. PATENT DOCUMENTS

| | | | |
|---|---|---|---|
| 6,663,871 B1 | 12/2003 | McMichael et al. | |
| 2010/0278904 A1* | 11/2010 | Holst | .............. A61K 39/12 424/450 |
| 2011/0293704 A1* | 12/2011 | Holst | .............. A61K 39/0011 424/450 |

FOREIGN PATENT DOCUMENTS

| | | |
|---|---|---|
| CN | 102292102 A | 12/2011 |
| JP | 2012509071 A | 4/2012 |
| WO | 2007062656 A2 | 5/2008 |
| WO | 2010057501 A1 | 5/2010 |
| WO | 2014141176 A | 9/2014 |
| WO | 2015082922 A1 | 6/2015 |
| WO | 2018037045 A1 | 3/2018 |

OTHER PUBLICATIONS

Tatsis et al. Virology 2007, vol. 367, pp. 156-167.*
Bull et al. PLoS One/www.plosone.org. Nov. 2007, Issue 11, e229, pp. 1-14.*
Shimada et al. Gen Therapy, 2009, vol. 16, pp. 218-228.*
Shachar et al. Immunity, 1995, vol. 3, No. 3, pp. 373-383.*
Alexander et al., "Enhanced vaccine-induced CD8+ T cell responses to malaria antigen ME-TRAP by fusion to MHC class ii invariant chain." PLOS ONE, vol. 9, No. 6, Jun. 2014 (Jun. 2014), pp. 1-15.
Capone et al., "Fusion of HCV nonstructural antigen to MHC class II-associated invariant chain enhances T-cell responses induced by vectored vaccines in nonhuman primates." Molecular Therapy : The Journal of the American Society of Gene Therapy, vol. 22, No. 5, May 2014 (May 2014), pp. 1039-1047.
Chen, et al., "Boosting immune response with the invariant chain segments via association with non-peptide binding region of major histocompatibility complex class II molecules", BMC Immunology, 13(1):55, 2012 (abstract).
Drillien, R., et al. Modified vaccinia virus Ankara induces moderate activation of human dendritic cells, Journal of General Virology, 2004, 85, 2167-2175.

(Continued)

*Primary Examiner* — Bao Q Li
(74) *Attorney, Agent, or Firm* — Lisa Matovcik

(57) ABSTRACT

The present application relates to novel administration regimens for poxviral vectors comprising nucleic acid constructs encoding antigenic proteins and invariant chains. In particular the use of said poxviral vectors for priming or for boosting an immune response is disclosed.

12 Claims, 4 Drawing Sheets
Specification includes a Sequence Listing.

(56) References Cited

OTHER PUBLICATIONS

Grujic, et al., "Fusion of a viral antigen to invariant chain leads to augmented T-cell immunity and improved protection in gene-gun DNA-vaccinated mice", Journal of General Virology, 90(2):414-422, 2009.

Staib et al. Construction and Isolation of Recombinant MVA in chapter 7 of Methods in Molecular Biology, published on 2004, vol. 269: Vaccinia Virus and Poxvirology: methods and protocols, Edited by S.N. Issacs Humana Press Inc., Totowa, HJ, pp. 77-99.

Vieng Fantao et al., "Comparison of functions of two active fragment vectors based on invariant chain in enhancing antibody secretion," Chinese Journal of Immunology, vol. 28, Aug. 20, 2012, pp. 728-732.

Sabarth, et al., "Comparison of single, homologous prime-boost and heterologous prime-boost immunization strategies against H5NI influenza virus in a mouse challenge model", Vaccine, 39(3):650-656, 2010.

Sorensen, et al., "Vaccination with the adenoviral vector encoding the tumor antigen directly linked to invariant chain induces potent CD4 + T-cell-independent DC8 + T-cell-mediated tumor control", European Journal of Immunology, vol. 39(10):2725-2736, 2009.

Schroeder, B., "The multifaceted roles of the invariant chain CD74—More than just a chaperone", Biochimica et Biophysica Acta, 1863(6): 1269-1281, 2016.

Gola, A., et al., "Prime and target immunization protects against liver-stage malaria in mice", Science and Translational Medicine, Research Article, 10, eaap9128, 1-11, 2018.

Borghese, F., et al., "CD74: an emerging opportunity as a therapeutic target in cancer and autoimmune disease", Expert Opinion on Therapeutic Targets, 15(3): 237-251, 2011.

Fougeroux, C., et al., "Modified MHC Class II—Associated invariant chain induces increased antibody responses against plasmodium falciparum antigens after adenoviral vaccination", The Journal of Immunology, 202: 2320-2331, 2019.

Holst, P. J., "Augmentation of adenovirus induced immune responses", PhD thesis, Faculty of Health Sciences, University of Copenhagen, 2008.

Capone, S., et al., "A short peptide from MHC class II invariant chain enhances CD8+ T cell responses by promoting antigen K48-linked ubiquitination and proteasomal degradation", Poster—EMBO Meeting, Paris, 2019.

Halbroth, B., et al., "Development of a molecular adjuvant to enhance antigen-specific CD8+ T Cell responses", Scientific Reports, 8: 1-14, 2018.

Shachar, I., et al., "Reconstitution of invariant chain function in transgenic mice in vivo by individual p. 31 and p. 41 soforms", Immunity, 3: 373-383, 1995.

International Search Report for PCT/IB2015/057085 dated May 1, 2016.

* cited by examiner

POXVIRAL VACCINES

CROSS-REFERENCE TO RELATED APPLICATIONS

This application is a divisional application of U.S. patent application Ser. No. 14/770,510, filed Aug. 26, 2015. The latter application is the US National Stage of International Application No. PCT/IB2014/059802, filed 14 Mar. 2014, which claims benefit of the filing date of PCT/EP2013/055409, filed 15 Mar. 2013, which is incorporated herein by reference in its entirety.

The present application relates to improved poxviral vaccines comprising nucleic acid constructs encoding antigenic proteins and invariant chains and novel administration regimens for such poxviral vectors. In particular the use of said poxviral vectors for priming or for boosting an immune response is disclosed.

BACKGROUND OF THE INVENTION

Infectious diseases are still a major threat to mankind. One way of preventing or treating infectious diseases is the artificial induction of an immune response by vaccination which is the administration of antigenic material to an individual such that an adaptive immune response against the respective antigen is developed. The antigenic material may be pathogens (e.g. microorganisms or viruses) which are structurally intact but inactivated (i.e. non-infective) or which are attenuated (i.e. with reduced infectivity), or purified components of the pathogen that have been found to be highly immunogenic. Another approach for inducing an immune response against a pathogen is the provision of expression systems comprising one or more vector encoding immunogenic proteins or peptides of the pathogen. Such vector may be in the form of naked plasmid DNA, or the immunogenic proteins or peptides may be delivered by using viral vectors, for example on the basis of modified vaccinia viruses (e.g. Modified Vaccinia Ankara; MVA) or adenoviral vectors. Such expression systems have the advantage of comprising well-characterized components having a low sensitivity against environmental conditions.

It is a particular aim when developing vector based expression systems that the application of these expression systems to a patient elicits an immune response which is protective against the infection by the respective pathogen. However, although inducing an immunogenic response against the pathogen, some expression systems are not able to elicit an immune response which is strong enough to fully protect against infections by the pathogen. Accordingly, there is still a need for improved expression systems which are capable of inducing a protective immune response against a pathogen as well as for novel administration regimens of known expression systems which elicit enhanced immune responses.

Antigens are peptide fragments presented on the surface of antigen presenting cells by MHC molecules. Antigens may be of foreign, i.e. pathogenic, origin or stem from the organism itself, the latter are referred to as self- or auto antigens. There are two classes of MHC molecules, MHC class I (MHC-I) and MHC-class-II (MHC-II). MHC-I molecules present fragments of peptides which are synthesized within the respective cell. MHC-II molecules present fragments of peptides which were taken up by phagocytosis and subsequently digested in the endosome. Typically, MHC-II molecules are only expressed by "professional" antigen presenting cells such as macrophages or dendritic cells. Antigens bound to MHC-II molecules are recognized by T-helper cells. The binding of the T-cell receptor of a T-helper cell to an antigen presented by a MHC-II molecule, together with cytokines secreted by the antigen-presenting cells, induces the maturation of an immature T-helper cell of the $TH_0$ phenotype into various types of effector cells.

The MHC-II molecules are membrane-bound receptors which are synthesized in the endoplasmatic reticulum and leave the endoplasmatic reticulum in a MHC class II compartment. In order to prevent endogenous peptides, i.e. self-antigens, from binding to the MHC-II molecule, the nascent MHC-II molecule combines with another protein, the invariant chain, which blocks the peptide-binding cleft of the MHC-II molecule. When the MHC class II compartment fuses to a late endosome containing phagocytosed and degraded proteins, the invariant chain is cleaved to leave only the CLIP region bound to the MHC-II molecule. In a second step, CLIP is removed by an HLA-DM molecule leaving the MHC-II molecule free to bind fragments of the foreign antigen. Said fragments are presented on the surface of the antigen-presenting cell once the MHC class II compartment fuses with the plasma membrane, thus presenting the foreign antigens to other cells, primarily T-helper cells.

It has been found previously (WO 2007/062656, which published as US 2011/0293704 and is incorporated by reference for the purpose of disclosing invariant chain sequences) that the fusion of the invariant chain to an antigen which is comprised by an expression system used for vaccination increases the immune response against said antigen, if it is administered with an adenovirus. Moreover, said adenoviral construct proved useful for priming an immune response in the context of a prime-boosting vaccination regimen (WO 2010/057501, which published as US 2010/0278904 and is incorporated by reference for the purpose of disclosing adenoviral vectors encoding invariant chain sequences). The present inventors have surprisingly found that the immune response against a given antigen can be even enhanced, if instead of an adenovirus a poxvirus is used for delivery of the invariant chain antigen fusion. In this way an immune response can be generated. It is particularly surprising that the poxviral vectors elicited this effect also when used for priming an immune response.

SUMMARY OF THE INVENTION

In a first aspect the present invention relates to a poxviral vector comprising a nucleic acid construct for use in priming or boosting an immune response, the nucleic acid construct comprising:
(i) a nucleic acid sequence encoding at least one antigenic protein or antigenic fragment thereof operatively linked to
(ii) a nucleic acid encoding at least one invariant chain.

In another aspect, the present invention relates to a vaccine combination comprising:
(a) a poxviral vector comprising a nucleic acid construct the nucleic acid construct comprising:
(i) a nucleic acid sequence encoding at least a first antigenic protein or antigenic fragment thereof operatively linked to
(ii) a nucleic acid encoding at least one invariant chain and
(b) a viral vector comprising a nucleic acid sequence encoding at least a second antigenic protein or antigenic fragment thereof
or
a second antigenic protein or antigenic fragment thereof
wherein at least one epitope of the first antigenic protein or antigenic fragment thereof is immunologically identical to the second antigenic protein or fragment thereof.

In yet another aspect, the present invention relates to the above-described vaccine combination, for use in a prime-boost vaccination regimen. Methods using such poxviral vectors and combinations are also provided.

DETAILED DESCRIPTION OF THE INVENTION

Unless defined otherwise, all technical and scientific terms used herein have the same meanings as commonly understood by one of ordinary skill in the art.

For example, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. All definitions provided herein in the context of one aspect of the invention also apply to the other aspects of the invention.

The problem underlying the present invention is solved by the embodiments characterized in the claims and in the description below.

In a first aspect the present invention relates to a poxviral vector comprising a nucleic acid construct for use in priming or boosting an immune response, the nucleic acid construct comprising:
  (i) a nucleic acid sequence encoding at least one antigenic protein or antigenic fragment thereof operatively linked to
  (ii) a nucleic acid encoding at least one invariant chain.

As used herein, the term "poxviral vector" refers to a naturally occurring member of the family poxviridae or a viral vector derived therefrom which is capable of introducing the nucleic acid construct into a cell of an individual. In the context of the present invention it is contemplated that the antigen and the invariant chain encoded by the introduced nucleic acid construct are expressed within said cell upon introduction by the poxviral vector.

The family poxviridae is characterized by a genome consisting of double-stranded DNA. Suitably, the poxviral vector belongs to the subfamily chordopoxvirinae, more preferably to a genus in said subfamily selected from the group consisting of orthopox, parapox, yatapox, avipox (preferably canarypox (ALVAC) or fowlpox (FPV)) and molluscipox. Even more preferably, the poxviral vector belongs to the orthopox and is selected from the group consisting of vaccinia virus, NYVAC (derived from the Copenhagen strain of vaccinia), modified vaccinia Ankara (MVA), cowpoxvirus and monkeypox virus. Most preferably, the poxviral vector is MVA.

A description of MVA can be found in Mayr A, Stickl H, Müller H K, Danner K, Singer H. "The smallpox vaccination strain MVA: marker, genetic structure, experience gained with the parenteral vaccination and behavior in organisms with a debilitated defense mechanism. "Abstammung, Eigenschaften and Verwendung des attenuierten Vaccinia-Stammes MVA." Zentralbl Bakteriol B. 1978 December; 167(5-6):375-90 and in Mayr, A., Hochstein-Mintzel, V. & Stickl, H. (1975). *Infection* 3, 6-14.

MVA is a highly attenuated strain of vaccinia virus that underwent multiple, fully characterised deletions during more than 570 passages in chick embryo fibroblast cells. These included host range genes and genes encoding cytokine receptors. The virus is unable to replicate efficiently in human and most other mammalian cells but the replication defect occurs at a late stage of virion assembly such that viral and recombinant gene expression is unimpaired making MVA an efficient single round expression vector incapable of causing infection in mammals.

In one embodiment, MVA is derived from the virus seed batch 460 MG obtained from 571th passage of Vaccinia Virus on CEF cells. In another embodiment, MVA is derived from the virus seed batch MVA 476 MG/14/78. In a further embodiment, MVA is derived or produced prior to 31 Dec. 1978 and is free of prion contamination.

Further poxviral vectors for the use of the invention have properties similar to MVA. In particular they are infectious but replication incompetent in humans. Due to this trait, it may be necessary to express proteins in trans for replication. Typically those proteins are stably or transiently expressed in a viral producer cell line, thereby allowing replication of the virus.

The term "nucleic acid" refers to a polymeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention nucleic acid molecules include but are not limited to ribonucleic acid (RNA) and deoxyribonucleic acid (DNA). Moreover, the term "polynucleotide" also includes artificial analogs of DNA or RNA, such as peptide nucleic acid (PNA).

The term "nucleic acid construct" refers to a nucleic acid which encodes at least one antigenic protein and at least one invariant chain. Suitably, said nucleic acid additionally comprises elements which direct transcription and translation of the polypeptides encoded by the nucleic acid construct. Such elements include promoter and enhancer elements to direct transcription of mRNA in a cell-free or a cell-based based system, for example a cell-based system. Suitably such promoter and/or enhancer is an endogenous promoter and/or enhancer of the poxviral vector. If the acid construct is provided as translatable RNA, it is envisioned that the nucleic acid construct comprises those elements that are necessary for translation and/or stabilization of RNAs encoding the at least one immunogenic polypeptide, e.g. polyA-tail, IRES, cap structures etc.

The term "substantially similar" if used in relation to nucleic acid sequences or amino acid sequences refers to a degree of sequence identity of more than 80%, more than 85%, more than 90%, more than 95%, more than 98%, or more than 99% of the respectively indicated reference nucleotide or amino acid sequence.

Residues in two or more polypeptides are said to "correspond" to each other if the residues or group of residues occupy (an) analogous position(s) in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, using standard settings, for example for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity oridentity between two aligned sequences drops to less than 30%, less than 20%, or less than 10% over a length of 10, 20 or 30 amino acids.

As outlined above it is contemplated that the vector of the present invention is a poxviral vector. Thus, if said poxviral vector is replication competent, the nucleic acid construct is comprised by a larger nucleic acid molecule which additionally includes nucleic acid sequences which are required for the replication of the viral vector and/or regulatory elements directing expression of the polypeptide encoded by the nucleic acid construct.

In one embodiment of the present invention the antigenic protein or antigenic fragment thereof and the invariant chain are comprised by a single open reading frame so that transcription and translation of said open reading frame results in a fusion protein comprising the antigenic protein or antigenic fragment thereof and the invariant chain.

The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e. by gene-technological means. An ORF codes for a protein where the amino acids into which it can be translated form a peptide-linked chain.

The terms "protein", "polypeptide" and "peptide" are used interchangeably herein and refer to any peptide-linked chain of amino acids, regardless of length, co-translational or post-translational modification.

The term "post-translational" used herein refers to events that occur after the translation of a nucleotide triplet into an amino acid and the formation of a peptide bond to the preceding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase.

The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupt the peptide bond formation resulting in two discreet translation products.

Proteins usable in the present invention (including protein derivatives, protein variants, protein fragments, protein segments, protein epitopes and protein domains) can be further modified by chemical modification. Hence, such a chemically modified polypeptide may comprise chemical groups other than the residues found in the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide. Such chemical modifications applicable to the variants usable in the present invention may occur co- or post-translational.

An "antigenic protein" as referred to in the present application is a polypeptide as defined above which contains at least one epitope. An "antigenic fragment" of an antigenic protein is a partial sequence of said antigenic protein comprising at least one epitope. For immunization purposes only those parts of a protein are relevant which elicit an immune response. Therefore, the nucleic acid construct does not need to encode the full-length antigenic protein as it is found in a pathogen or a cancer cell. A shortened fragment of such a protein is sufficient as long as its amino acid sequence comprises the epitope or epitopes responsible for the recognition of the antigenic protein by the immune system.

The term "epitope" also known as antigenic determinant, as used in the context of the present invention is that part of a polypeptide which is recognized by the immune system. Suitably, this recognition is mediated by the binding of antibodies, B cells, or T cells to the epitope in question. The epitopes bound by antibodies or B cells are referred to as "B cell epitopes" and the epitopes bound by T cells are referred to as "T cell epitopes". In this context, the term "binding" relates to a specific binding, which is defined as a binding with an association constant between the antibody or T cell receptor (TCR) and the respective epitope of $1 \times 10^5$ $M^{-1}$ or higher, or of $1 \times 10^6$ $M^{-1}$, $1 \times 10^7$ $M^{-1}$, $1 \times 10^8$ $M^{-1}$ or higher. The skilled person is well aware how to determine the association constant (see e.g. Caoili, S. E. (2012) Advances in Bioinformatics Vol. 2012). Suitably, the specific binding of antibodies to an epitope is mediated by the Fab (fragment, antigen binding) region of the antibody, specific binding of a B-cell is mediated by the Fab region of the antibody comprised by the B-cell receptor and specific binding of a T-cell is mediated by the variable (V) region of the T-cell receptor. T cell epitopes are presented on the surface of an antigen presenting cell, where they are bound to Major Histocompatiblilty (MHC) molecules. There are at least three different classes of MHC molecules termed MHC class I, II and III molecules, respectively. Epitopes presented through the MHC-I pathway elicit a response by cytotoxic T lymphocytes ($CD8^+$ cells), while epitopes presented through the MHC-II pathway elicit a response by T-helper cells ($CD4^+$ cells). T cell epitopes presented by MHC Class I molecules are typically peptides between 8 and 11 amino acids in length and T cell epitopes presented by MHC Class II molecules are typically peptides between 13 and 17 amino acids in length. MHC Class III molecules also present non-peptidic epitopes as glycolipids. Accordingly, the term "T cell epitope" refers to a 8 to 11 or 13 to 17 amino acid long peptide that can be presented by either a MHC Class I or MHC Class II molecule.

Epitopes usually consist of chemically active surface groupings of molecules such as amino acids or sugar side chains and usually have specific three-dimensional structural characteristics, as well as specific charge characteristics. The term "epitope" refers to conformational as well as non-conformational epitopes. Conformational and non-conformational epitopes are distinguished in that the binding to the former but not the latter is lost in the presence of denaturing solvents. T cell epitopes are non-conformational, i.e. they are linear, while B cell epitopes can be conformational or non-conformational. Linear B-cell epitopes typically vary between 5 to 20 amino acids in length.

An antigenic protein according to the present invention is derived from a pathogen selected from the group consisting of viruses, bacteria, protozoa and multicellular parasites. In an alternative embodiment of the present invention the antigenic protein is a polypeptide or fragment of a polypeptide expressed by a cancer cell.

Antigenic proteins or antigenic fragments thereof induce a B-cell response or a T-cell response or a B-cell response and a T-cell response. Accordingly, antigenic proteins or antigenic fragments comprise at least one T cell epitope and/or at least one B cell epitope.

In a certain exemplary embodiment of the present invention, the antigenic protein encoded by the vector is derived from hepatitis C virus (HCV). The HCV genome consists of a single RNA strand about 9.5 kb in length which encodes a precursor polyprotein of about 3000 amino acids. (Choo et al. (1989) Science 244, 362-364; Choo et al. (1989) Science 244, 359-362; Takamizawa et al. (1991) J. Virol. 65, 1105-1113) The HCV polyprotein contains the viral proteins in the order: C-E1-E2-p7-NS2-NS3-NS4A-NS4B-NS5A-NS5B. Individual viral proteins are produced by proteolysis of the HCV polyprotein. Host cell proteases release the putative structural proteins C, E1, E2, and p7, and create the N-terminus of NS2 at amino acid 810. (Mizushima et al. (1994) J. Virol. 65, 2731-2734; Hijikata et al. (1993) P.N.A.S. USA 90, 10773-10777)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui et al. (1993) J. Virol. 67, 1385-1395, Hijikata et al. (1993) P.N.A.S. USA 90, 10773-10777.) A distinct serine protease located in the N-terminal domain of NS3 is responsible for proteolytic cleavages at the NS3/NS4A, NS4A/NS4B, NS4B/NS5A and NS5A7NS5B junctions. (Bartenschlager et al. (1993) J. Virol. 67, 3835-3844; Grakoui et al., (1993) Proc. Natl. Acad. Sci. USA 90, 10583-10587, Tomei et al. (1993) Virol. 67, 4017-4026) NS4A provides a cofactor for NS3 activity. (Failla et al. (1994) J. Virol. 68, 3753-3760; De Francesco et al, U.S. Pat. No. 5,739,002.). NS5A is a highly phosphorylated protein conferring interferon resistance. (De Francesco et al., (2000) Semin. Liver Dis., 20(1), 69-83; Pawlotsky (1999) Viral Hepat. Suppl. 1, 47-48). NS5B provides an RNA-dependent RNA polymerase. (De Francesco et al, International Publication Number WO 96/37619, Behrens et al, EMBO 15, 12-22, 1996, Lohmann et al., Virology 249, 108-118, 1998.)

In one non-limiting exemplary embodiment, the antigenic protein is a Met-NS3-NS4A-NS4B-NS5A-NS5B polypeptide containing an inactive NS5B RNA-dependent RNA polymerase region. For example, said antigenic protein has an amino acid sequence substantially similar to the sequence defined by SEQ ID NO: 11 and has sufficient protease activity to process itself to produce at least a polypeptide substantially similar to the NS5B region present in SEQ ID NO: 11. The sequence of this antigenic protein has been published in WO 2003/031588, which published as US 2004/0247615 and is incorporated by reference for the purpose of disclosing HCV polypeptides. The produced polypeptide corresponding to NS5B is enzymatically inactive. In a further embodiment, the HCV polypeptide has sufficient protease activity to produce polypeptides substantially similar to the NS3, NS4A, NS4B, NS5A, and NS5B regions present in SEQ ID NO: 11.

In one embodiment, the degree of sequence identity to the sequence according to SEQ ID NO: 11 is more than 80%, more than 85%, more than 90%, more than 95% or more than 98% of the sequence defined by SEQ ID NO: 11. However, in some embodiments, the sequence of the antigenic protein has more than 99% sequence identity to the sequence defined by SEQ ID NO: 11 or is identical to it.

The term "invariant chain", also known as "Ii" or "CD74" refers to a non-polymorphic type II integral membrane protein. The protein has multiple functions in lymphocyte maturation and adaptive immune responses; in particular Ii ensures the targeting of newly synthesized MCH II to the endocytic pathway, where the complex can meet antigenic peptides. (Pieters J. (1997) Curr. Opin. Immunol., 9: 8996). Additionally, Ii has been shown to function as an MHC class I chaperone (Morris et al. (2004) Immunol. Res., 30: 171-179) and, by its endosomal targeting sequence, to facilitate stimulation of $CD4^+$, but not $CD8^+$ T-cells directed against covalently linked antigen (Diebold et al. (2001) Gene Ther. 8: 487-493).

For human invariant chain four different isoforms are known, generally termed p33, p35, p41 and p43 (Strubin et al., 1986, EMBO Journal, 5: 3483-3488). SEQ ID NO: 1 and SEQ ID NO: 2 correspond to the amino acid sequence and the nucleic acid sequence of human invariant chain p35 isoform. With respect to human p33 and p41 the human p35 and p43 isoforms contain an additional 16 residues at the N-terminus due to alternative initiation of translation. Compared to human p33 and p35 the human p41 and p43 isoforms comprise an additional domain (alternative splicing of exon 6b) inserted in frame in the C-terminal region of the invariant chain. SEQ ID NO: 5 and SEQ ID NO: 6 correspond to the amino acid sequence and the nucleic acid sequence of human invariant chain p43 isoform. The sequence of an additional human isoform c lacking two exons relative to human p33 and p35 is available in Genbank (Accession BC024272). SEQ ID NO: 9 and SEQ ID NO: 10 correspond to the amino acid sequence and the nucleic acid sequence of human invariant chain c isoform.

TABLE 1

Overview over the variants of human invariant chain

| Isoform | 16 AA at N-terminus | Additional domain | SEQ ID NO: (peptide, nucleic acid) |
|---------|---------------------|-------------------|-------------------------------------|
| P33 | − | − | — |
| P35 | + | − | 1, 2 |
| P41 | − | + | — |
| P43 | + | + | 5, 6 |
| c | + | − | 9, 10 |

For murine invariant chain only two isoforms (p31 and p41) are known corresponding to the human invariant chain isoforms p33 and p41. SEQ ID NO: 3 and SEQ ID NO: 4 correspond to the amino acid sequence and the nucleic acid sequence of murine invariant chain p31 isoform. SEQ ID NO: 7 and SEQ ID NO: 8 correspond to the amino acid sequence and the nucleic acid sequence of murine invariant chain p41 isoform. A schematic overview over the different isoforms is shown in FIG. 4.

In one embodiment, the invariant chain used in the present invention is substantially similar to the invariant chain according to SEQ ID NO: 1 or 3.

The invariant chain comprises several domains: a cytosolic domain which includes a sorting (targeting) peptide (also known as the lysosomal targeting sequence) (positions 17 to 46 in human invariant chain SEQ ID NO: 1, positions 1 to 29 in the murine invariant chain SEQ ID NO: 3) preceded by an ER retention signal in the human invariant chain p35 and p43 variants (positions 1 to 16 in human invariant chain SEQ ID NO: 1), a transmembrane domain (signal anchor, positions 47 to 72 in human invariant chain SEQ ID NO: 1, positions 30 to 55 in the murine invariant chain SEQ ID NO: 3), and a luminal domain which in itself comprises a KEY region (positions 93 to 96 in human invariant chain SEQ ID NO: 1, positions 76 to 79 in the murine invariant chain SEQ ID NO: 3), an adjacent CLIP region (positions 97 to 120 in human invariant chain SEQ ID NO 1, positions 80 to 103 in the murine invariant chain SEQ ID NO: 3). The CLIP region comprises a core CLIP peptide (positions 103 to 117 in human invariant chain SEQ ID NO: 1, positions 86 to 100 in the murine invariant chain SEQ ID NO: 3) and a trimerization domain (positions 134 to 208 in human invariant chain SEQ ID NO: 1, positions 117 to 191 in the murine invariant chain SEQ ID NO: 3; Mittendorf et al., (2009) Expert Opin. Biol. Ther., 9:71-78; Strumptner-Cuvelette and Benaroch, 2002, Biochem. Biophys. Acta, 1542: 1-13). The remainder of the luminal domain comprises two highly flexible regions situated between the transmembrane and KEY region (positions 73 to 92 in human invariant chain SEQ ID NO: 1, positions 56 to 75 in the murine invariant chain SEQ ID NO: 3) or downstream the trimerization domain (positions 209 to 232 in human invariant chain SEQ ID NO: 1, positions 192 to 215 in the murine invariant chain SEQ ID NO: 3). Invariant chain has been characterized in several organisms such as chicken, cow, dog, mouse, rat and human.

In one embodiment, the invariant chain is of vertebrate origin, of avian or mammalian origin, or further, it is selected from the group consisting of invariant chains derived from chicken, cow, dog, mouse, rat, non-human primate and human. In a further embodiment, it is of human or murine origin, for example, the human invariant chain has an amino acid sequence as defined by SEQ ID NO: 1. Said polypeptide is in one embodiment encoded by a nucleic acid sequence as given in SEQ ID NO: 2. In another embodiment, the murine invariant chain has an amino acid sequence as defined by SEQ ID NO: 3. Said polypeptide is in one embodiment encoded by a nucleic acid sequence as given in SEQ ID NO: 4.

The term "invariant chain" also comprises variants of the above-described polypeptides characterized by deletions of parts of the amino acid sequences of naturally occurring invariant chains or of invariant chains substantially similar to the naturally occurring invariant chains or by their substitution with other sequences. Exemplary variants are given below.

In one particular variant of the invariant chain, the endogenous KEY-region which consists of the LRMK amino acid residues is deleted or is substituted by a different amino acid sequence. For example, the LRMK amino acid residues or corresponding residues are deleted. Deletion of the LRMK amino acid residues may be complete (involving all LRMK amino acid residues) or partial (involving at least one LRMK amino acid residue). Complete deletion of all LRMK amino acid residues is envisioned. Further, at least one or all of the LRMK amino acid residues are substituted by different amino acid residues.

In yet another exemplary variant the methionines in positions 107 and 115 of the human invariant chain according to SEQ ID NO: 1 or the methionines in positions 90 and 98 of the murine invariant chain according to SEQ ID NO: 3 or the methionines corresponding to these positions in other invariant chains are substituted by other amino acids. Suitably, the methionine is substituted.

In yet another exemplary variant, the invariant chain is N-terminally truncated, for example to such an extent that the N-terminus up to the transmembrane region is removed. Accordingly, in a further embodiment, the invariant chain according to Seq ID NO: 1 46 amino acids or less of the N-terminus are truncated, 41 amino acids or less are truncated, or 36 amino acids or less are truncated. Accordingly it is also contemplated that for the invariant chain according to Seq ID NO: 3 30 amino acids or less of the N-terminus are truncated, 25 amino acids or less are truncated, or 20 amino acids or less are truncated. For one embodiment of the invariant chain according to SEQ ID NO: 1, the first 16 amino acid residues of the human invariant chain are deleted. It is also possible that at least one, but not all of the first 16 amino acid residues are deleted. Furthermore, it is possible that at least one, or all of the first 16 amino acid residues of the human invariant chain (SEQ ID NO: 1) are substituted by other amino acid residues.

In yet another variant, at least one signal peptide for expression in the lumen of the endoplasmatic reticulum is added to the N-terminus of the invariant chain, for example to an N-terminally truncated version of the invariant chain which—due to the N-terminal truncation—lacks the transmembrane region.

In yet another variant of the invariant chain at least one CLIP region is added to or replaces the endogenous CLIP region of the respective invariant chain. In the human invariant chain according to SEQ ID NO: 1 the CLIP region spans positions 97 to 120 and in the murine invariant chain according to SEQ ID NO 3 it spans positions 80 to 103. Thus, the skilled person can easily determine the amino acid residues corresponding to the CLIP region in the invariant chain according to SEQ ID NO: 1 and 3. In a further embodiment, the complete endogenous CLIP region is deleted or replaced. However, the deletion or replacement of at least one amino acid residue belonging to the endogenous CLIP region is also contemplated.

The term "invariant chain" also refers to fragments of the invariant chains and their variants described above, for example, the invariant chains having amino acid sequences according to SEQ ID NO: 1 or 3 or encoded by nucleic acid sequences according SEQ ID NO: 2 or 4. It is to be understood that due to the degenerated nature of the genetic code, one amino acid may be encoded by more than one codon. For example, the amino acid isoleucine may be encoded by the codons AUU, AUC or AUA. Therefore, the present invention also encompasses all variants of the aforementioned nucleic acid sequences which encode the amino acid sequences defined by SEQ ID NOs: 1 or 3 irrespective of the specific nucleic acid sequence. Since different organisms utilize different codons with different efficiency, it may be advantageous to adapt the codon usage in a nucleotide sequence to the intended host organism. In one embodiment, the fragment is a fragment of at least 40, 50, 60, 70, 80, 90, 10, 110, 120, 130, 140, 150, 160, 170, 180, 190, 200 or 210 amino acid residues of a wild-type invariant chain or a variant thereof as defined above.

Moreover, the term "invariant chain" refers to polypeptides having at least 80%, 85%, 90%, 91%, 92%, 93%, 94%, 95%, 96%, 97%, 98%, 99%, 99.5%, 99.8% or 99.9% sequence identity with any of the above described wild-type invariant chains, variants or fragments thereof. Methods for determining the sequence identity between two different polypeptides are well known in the art. The similarity of nucleotide and amino acid sequences, i.e. the percentage of sequence identity, can be determined via sequence alignments. Such alignments can be carried out with several art-known algorithms, for example with the mathematical algorithm of Karlin and Altschul (Karlin & Altschul (1993) Proc. Natl. Acad. Sci. USA 90: 5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80) available e.g. on www.ebi.ac.uk/Tools/clustalw/ or on www.ebi.ac.uk/Tools/clustalw2/index.html or on npsa-pbil-.ibcp.fr/cgi-bin/npsa_automat.pl?page=/NPSA/npsa_clustalw.html. Preferred parameters used are the default parameters as they are set on www.ebi.ac.uk/Tools/clustalw/ or www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410.

To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1: I54-I62) or Markov random fields. When percentages of sequence identity are referred to in the present application, these percentages are calculated in relation to the full length of the longer sequence, if not specifically indicated otherwise.

The term "priming an immune response" refers to the first encounter of the immune system with the at least one antigenic protein or antigenic fragment thereof and the subsequent induction of an antigen-specific immune response within a defined period of time. Said period of time is, for example, at least 1 year, at least 2 years, at least 3 years, at least 5 years or at least 10 years prior to the priming. In one embodiment, encounters of the individual's or subject's immune system with the antigenic protein or antigenic fragment thereof of which do not induce an antigen-specific immune response are not considered as "priming an immune response". For example, encounters of the individual's immune system with the antigenic protein or antigenic fragment thereof which do not induce lasting immunity are not considered as "priming an immune response" according to the present invention. In a further embodiment, the induction of lasting immunity is mediated by the generation of memory B cells and/or memory T cells. In the case of cancer, for example, a specific antigen may be expressed by the cancer cells without eliciting an immune response. The mere presence of this antigen is not a "priming of an immune response" against said antigen as understood by the present application. In one embodiment, the individual or subject has not been deliberately immunized with the antigenic protein or antigenic fragment thereof or a vector comprising a nucleic acid encoding such a protein or fragment with the aim of treating or preventing a disease in the period of time given before.

However, the term "priming an immune response" refers to any previous contact of the individual with a pathogen naturally comprising said antigenic protein or antigenic fragment thereof provided that said contact was not artificially induced for medical purposes. In particular it is envisaged by the present application that the individual may already have been infected with the aforementioned pathogen provided that said infection was not artificially induced for medical purposes. At the time the priming of the immune response takes place, the infection of the individual may still be present or it may already have been eliminated. Similarly, in the case of cancer, it is envisaged that the individual or subject to be immunized with the poxviral vector of the present invention already suffers from the cancer expressing the antigenic protein or antigenic fragment thereof which is comprised by the nucleic acid construct of the present invention.

The patient or subject to be immunized with a poxviral vector according to the present invention is, for example, a mammal or a bird, more specifically a primate, mouse, rat, sheep, goat, cow, pig, horse, goose, chicken, duck or turkey and, most specifically, a human.

The poxviral vector comprising a nucleic acid construct as defined above is, for example, used in a prime-boost vaccination regimen.

In many cases, a single administration of a vaccine is not sufficient to generate the number of long-lasting immune cells which is required for effective protection in case of future infection of the pathogen in question, protect against diseases including tumour diseases or for therapeutically treating a disease, like tumour disease. Consequently, repeated challenge with a biological preparation specific for a specific pathogen or disease is required in order to establish lasting and protective immunity against said pathogen or disease or to cure a given disease. An administration regimen comprising the repeated administration of a vaccine directed against the same pathogen or disease is referred to in the present application as "prime-boost vaccination regimen". In one embodiment, a prime-boost vaccination regimen involves at least two administrations of a vaccine or vaccine composition directed against a specific pathogen, group of pathogens or diseases. The first administration of the vaccine is referred to as "priming" and any subsequent administration of the same vaccine or a vaccine directed against the same pathogen as the first vaccine is referred to as "boosting". Thus, in a further embodiment of the present invention the prime-boosting vaccination regimen involves one administration of the vaccine for priming the immune response and at least one subsequent administration for boosting the immune response. It is to be understood that 2, 3, 4 or even 5 administrations for boosting the immune response are also contemplated by the present invention.

The period of time between prime and boost is, optionally, 1 week, 2 weeks, 4 weeks, 6 weeks or 8 weeks. More particularly, it is 4 weeks or 8 weeks. If more than one boost is performed, the subsequent boost is administered 1 week, 2 weeks, 4 weeks, 6 weeks or 8 weeks after the preceding boost. For example, the interval between any two boosts is 4 weeks or 8 weeks.

Prime-boost vaccination regimens may be homologous or heterologous. In homologous prime-boost regimens both the priming and the at least one boosting is performed using the same means of administration of the antigenic protein or antigenic fragment thereof, i.e. priming and boosting are performed using a polypeptide or priming and boosting are performed using a nucleic acid construct comprised by the same vector. In the context of the present invention a homologous prime-boost vaccination regimen would comprise the use of the poxviral vector of the invention both for priming as well as for boosting the immune response. A heterologous prime-boosting regimen involves the use of different means for priming and for boosting the immune response. In the context of the present invention, a heterologous prime-boosting regimen would comprise a poxviral vector as described above for the priming of an immune response and a different vector or a peptide vaccine for the boosting of the immune response.

Alternatively, a heterologous prime-boosting regimen would comprise a different vector or a peptide vaccine for the priming of an immune response and a poxviral vector as described above for the boosting of the immune response.

In one embodiment of the present invention the prime-boosting vaccination regimen is homologous.

In another embodiment of the present invention the prime-boosting vaccination regimen is heterologous.

In one heterologous prime boosting regimen a poxviral vector as described above is used for the boosting of the immune response and a different vector or a peptide vaccine is used for the priming of the immune response. In another embodiment, heterologous prime boosting regimen, a poxviral vector as described above is used for the priming of the immune response and a different vector or a peptide vaccine is used for the boosting of the immune response.

In another embodiment the heterologous prime-boosting regimen would comprise an adenovirus vector for the priming of an immune response and a poxviral vector as described above for the boosting of the immune response.

In yet another embodiment, the heterologous prime boosting regimen would comprise an poxviral vector as described above for the priming of an immune response and a adenoviral vector for the boosting of the immune response.

For all prime-boosting vaccination regimens it is envisioned that the antigenic proteins or antigenic peptides used for boosting the immune response are immunologically identical to the antigenic protein or antigenic fragment thereof used for priming the immune response. It is to be understood that the antigenic protein or antigenic fragment thereof may be administered as a polypeptide ("peptide vaccine") or that it may be encoded by a nucleic acid molecule administered to the individual in question. In the latter case, the antigenic protein or antigenic polypeptide which elicits the desired immune response is expressed in the cells of immunized individual.

Two or more antigenic proteins or antigenic fragments thereof are "immunologically identical" if they are recognized by the same antibody, T-cell or B-cell. The recognition of two or more immunogenic polypeptides by the same antibody, T-cell or B-cell is also known as "cross reactivity" of said antibody, T-cell or B-cell. In one embodiment, the recognition of two or more immunologically identical polypeptides by the same antibody, T-cell or B-cell is due to the presence of identical or similar epitopes in all polypeptides. Similar epitopes share enough structural and/or charge characteristics to be bound by the Fab region of the same antibody or B-cell receptor or by the V region of the same T-cell receptor. The binding characteristics of an antibody, T-cell receptor or B-cell receptor are, for example, defined by the binding affinity of the receptor to the epitope in question. Two immunogenic polypeptides are "immunologically identical" as understood by the present application if the affinity constant of polypeptide with the lower affinity constant is at least 30%, at least 40%, at least 50%, at least 60%, at least 70%, at least 80%, at least 90%, at least 95% or at least 98% of the affinity constant of the polypeptide with the higher affinity constant. Methods for determining the binding affinity of a polypeptide to a receptor such as equilibrium dialysis or enzyme linked immunosorbent assay (ELISA) are well known in the art.

In one embodiment, two or more "immunologically identical" polypeptides comprise at least on identical epitope. The strongest vaccination effects can usually be obtained, if the immunogenic polypeptides comprise identical epitopes or if they have an identical amino acid sequence.

In one embodiment, the use of the poxviral vector as described above for the priming of an immune response will establish protective immunity against a pathogen or disease or will lead to eradication of the disease.

In one embodiment, the poxviral vector is administered via intranasal, intramuscular, subcutaneous, intradermal, intragastric, oral and topical routes.

An "intranasal administration" is the administration of a vector of the present invention to the mucosa of the complete respiratory tract including the lung. More particularly, the composition is administered to the mucosa of the nose. In one embodiment, an intranasal administration is achieved by means of instillation, spray or aerosol. In a further embodiment, said administration does not involve perforation of the mucosa by mechanical means such as a needle.

The term "intramuscular administration" refers to the injection of a vector into any muscle of an individual. Exemplary intramuscular injections are administered into the deltoid, vastus lateralis or the ventrogluteal and dorsogluteal areas.

The term "subcutaneous administration" refers to the injection of a vector into the hypodermis.

The term "intradermal administration" refers to the injection of a vector into the dermis between the layers of the skin.

The term "oral administration" refers to the administration of a vector via the mouth to the gastric system.

A "topical administration" is the administration of the vector to any part of the skin without penetrating the skin with a needle or a comparable device. The vector may also be administered topically to the mucosa of the mouth, nose, genital region and rectum.

In another aspect, the present invention relates to a vaccine combination comprising:
(a) a poxviral vector comprising a nucleic acid construct, the nucleic acid construct comprising:
  (i) a nucleic acid sequence encoding at least a first antigenic protein or antigenic fragment thereof operatively linked to
  (ii) a nucleic acid encoding at least one invariant chain and
(b) a vector comprising a nucleic acid sequence encoding at least a second antigenic protein or antigenic fragment thereof
or
  a second antigenic protein or antigenic fragment thereof
or
  viral like particles
wherein at least one epitope of the first antigenic protein or antigenic fragment thereof is immunologically identical to the at least second antigenic protein or fragment thereof.

The term "vaccine" refers to a biological preparation which induces or improves immunity to a specific disease. Said preparation may comprise a killed or an attenuated living pathogen. It may also comprise one or more compounds derived from a pathogen suitable for eliciting an immune response. In one embodiment, said compound is a polypeptide which is substantially identical or immunologically identical to a polypeptide of said pathogen. In another embodiment, the vaccine comprises a nucleic acid construct which encodes an immunogenic polypeptide which is substantially identical or immunologically identical to a polypeptide of said pathogen. In the latter case, it is also contemplated that the polypeptide is expressed in the individual treated with the vaccine. The principle underlying vaccination is the generation of an immunological "memory". Challenging an individual's immune system with a vaccine induces the formation and/or propagation of immune cells which specifically recognize the compound comprised by the vaccine. At least a part of said immune cells remains viable for a period of time which can extend to 10, 20 or 30 years after vaccination. If the individual's immune system encounters the pathogen from which the compound capable of eliciting an immune response was derived within the aforementioned period of time, the immune cells generated by vaccination are reactivated and enhance the immune response against the pathogen as compared to the immune response of an individual which has not been challenged with the vaccine and encounters immunogenic compounds of the pathogen for the first time.

As used herein, the term "vector" refers to at least one polynucleotide or to a mixture of at least one polynucleotide and at least one protein which is capable of introducing the polynucleotide comprised therein into a cell. Moreover, the term "vector" may also refer to at least one polynucleotide formulated with a preparation of liposomes or lipid nanoparticles which is capable of transfecting a cell with the at least one polynucleotide as described, e.g. by Geall et al., 2012, PNAS, 109:14604-14609.

At least one polynucleotide comprised by the vector consists of or comprises at least one nucleic acid construct encoding at least one immunogenic protein. In addition to the polynucleotide consisting of or comprising the nucleic acid construct of the present invention additional polynucleotides and/or polypeptides may be introduced into the cell. The addition of additional polynucleotides and/or polypeptides is also contemplated if said additional polynucleotides and/or polypeptides are required to introduce the nucleic acid construct of the present invention into the cell or if the introduction of additional polynucleotides and/or polypeptides increases the expression of the immunogenic polypeptide encoded by the nucleic acid construct of the present invention.

In the context of the present invention it is envisioned that the antigenic protein or the antigenic fragment thereof encoded by the introduced nucleic acid construct are expressed within the cell upon introduction of the vector or vectors. Examples of suitable vectors include but are not limited to plasmids, cosmids, phages, viral vectors, lipid nanoparticles or artificial chromosomes.

In an embodiment of the present invention the viral vector is selected from the group consisting of adenovirus vectors, adeno-associated virus (AAV) vectors (e.g., AAV type 5 and type 2), alphavirus vectors (e.g., Venezuelan equine encephalitis virus (VEE), sindbis virus (SIN), semliki forest virus (SFV), and VEE-SIN chimeras), herpes virus vectors (e.g. vectors derived from cytomegaloviruses, like rhesus cytomegalovirus (RhCMV), arena virus vectors (e.g. lymphocytic choriomeningitis virus (LCMV) vectors), measles virus vectors, poxvirus vectors, paramixovirus vector, baculovirus vectot vesicular stomatitis virus vectors, retrovirus, lentivirus, viral like particles, and bacterial spores.

In a further embodiment, vectors are adenoviral vectors, in particular adenoviral vectors derived from human or non-human great apes. Exemplary great apes from which the adenoviruses are derived are Chimpanzee (*Pan*), Gorilla (Gorilla) and orangutans (Pongo), for example Bonobo (*Pan paniscus*) and common Chimpanzee (*Pan troglodytes*). Typically, naturally occurring non-human great ape adenoviruses are isolated from stool samples of the respective great ape. Specifically, vectors are non-replicating adenoviral vectors based on hAd5, hAd11, hAd26, hAd35, hAd49, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd 73, ChAd82, ChAd83, ChAd146, ChAd147, PanAd1, PanAd2, and PanAd3 vectors or replication-competent Ad4 and Ad7 vectors. The human adenoviruses hAd4, hAd5, hAd7, hAd11, hAd26, hAd35 and hAd49 are well known in the art. Vectors based on naturally occurring ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in detail in WO 2005/071093, which published as US 20110217332 and is incorporated by reference as to the adenoviral vectors described therein. Vectors based on naturally occurring PanAd1, PanAd2, PanAd3, ChAd55, ChAd73, ChAd83, ChAd146, and ChAd147 are described in detail in WO 2010/086189, which published as US 20120027788 and is incorporated by reference as to the adenoviral vectors described therein.

In another embodiment, the second antigenic protein or antigenic fragment thereof is immunologically identical to the antigenic protein or antigenic fragment thereof encoded by the nucleic acid construct comprised by the poxviral vector.

In another embodiment of the present invention, the vector is present as naked DNA. The term "naked DNA" refers to any nucleic acid molecule, DNA or RNA, which does not encode proteins of a viral vector but encodes at least one antigenic protein or fragment thereof. It is contemplated that naked DNA is not associated with any polypeptides, in particular not with polypeptides of viral origin. For example, naked DNA is present as plasmid, cosmid or as an artificial chromosome. In a further embodiment, the naked DNA encodes a polypeptide which is immunologically identical to the antigenic protein or antigenic fragment thereof encoded by the nucleic acid construct comprised by the poxviral vector.

The term "viral like particle" (VLP) refers to assemblies comprising viral proteins but no nucleic acid. VLPs can be produced by expressing viral surface proteins in suitable producer cell-lines. The lack of nucleic acid, and thus genetic information, renders VLP non-infectious, thus creating a safe vaccine. For example, the VLP comprises a polypeptide which is immunologically identical to the antigenic protein or antigenic fragment thereof encoded by the nucleic acid construct comprised by the poxviral vector.

In a certain embodiment of the present invention the above-described vaccine combination is used in a prime-boost vaccination regimen. In a first embodiment of this prime-boost vaccination regimen the poxviral vector is used for priming the immune response and the viral vector or antigenic protein or antigenic fragment thereof is used for boosting the immune response. In another embodiment of the prime-boost vaccination regimen, the viral vector or antigenic protein or antigenic fragment thereof is, used for priming the immune response and the poxviral vector is used for boosting the immune response.

In an embodiment of the present invention,
the immune response is primed by intranasal administration and the immune response is boosted by at least one intramuscular administration;
the immune response is primed by intranasal administration and the immune response is boosted by at least one subcutaneous administration;
the immune response is primed by intranasal administration and the immune response is boosted by at least one intradermal administration;
the immune response is primed by intranasal administration and the immune response is boosted by at least one intragastric administration;
the immune response is primed by intranasal administration and the immune response is boosted by at least one oral administration;
the immune response is primed by intranasal administration and the immune response is boosted by at least one topical administration;
the immune response is primed by intranasal administration and the immune response is boosted by at least one intranasal administration;
the immune response is primed by intramuscular administration and the immune response is boosted by at least one intramuscular administration;
the immune response is primed by intramuscular administration and the immune response is boosted by at least one subcutaneous administration;
the immune response is primed by intramuscular administration and the immune response is boosted by at least one intradermal administration;
the immune response is primed by intramuscular administration and the immune response is boosted by at least one intragastric administration;
the immune response is primed by intramuscular administration and the immune response is boosted by at least one oral administration;
the immune response is primed by intramuscular administration and the immune response is boosted by at least one topical administration;
the immune response is primed by intramuscular administration and the immune response is boosted by at least one intranasal administration;
the immune response is primed by subcutaneous administration and the immune response is boosted by at least one intramuscular administration;
the immune response is primed by subcutaneous administration and the immune response is boosted by at least one subcutaneous administration;
the immune response is primed by subcutaneous administration and the immune response is boosted by at least one intradermal administration;
the immune response is primed by subcutaneous administration and the immune response is boosted by at least one intragastric administration;
the immune response is primed by subcutaneous administration and the immune response is boosted by at least one oral administration;
the immune response is primed by subcutaneous administration and the immune response is boosted by at least one topical administration;
the immune response is primed by subcutaneous administration and the immune response is boosted by at least one intranasal administration;
the immune response is primed by intradermal administration and the immune response is boosted by at least one intramuscular administration;
the immune response is primed by intradermal administration and the immune response is boosted by at least one subcutaneous administration;
the immune response is primed by intradermal administration and the immune response is boosted by at least one intradermal administration;
the immune response is primed by intradermal administration and the immune response is boosted by at least one intragastric administration;
the immune response is primed by intradermal administration and the immune response is boosted by at least one oral administration;
the immune response is primed by intradermal administration and the immune response is boosted by at least one topical administration;
the immune response is primed by intradermal administration and the immune response is boosted by at least one intranasal administration;
the immune response is primed by intragastric administration and the immune response is boosted by at least one intramuscular administration;
the immune response is primed by intragastric administration and the immune response is boosted by at least one subcutaneous administration;
the immune response is primed by intragastric administration and the immune response is boosted by at least one intradermal administration;
the immune response is primed by intragastric administration and the immune response is boosted by at least one intragastric administration;
the immune response is primed by intragastric administration and the immune response is boosted by at least one oral administration;
the immune response is primed by intragastric administration and the immune response is boosted by at least one topical administration;
the immune response is primed by intragastric administration and the immune response is boosted by at least one intranasal administration;
the immune response is primed by oral administration and the immune response is boosted by at least one intramuscular administration;
the immune response is primed by oral administration and the immune response is boosted by at least one subcutaneous administration;
the immune response is primed by oral administration and the immune response is boosted by at least one intradermal administration;
the immune response is primed by oral administration and the immune response is boosted by at least one intragastric administration;
the immune response is primed by oral administration and the immune response is boosted by at least one oral administration;
the immune response is primed by oral administration and the immune response is boosted by at least one topical administration;
the immune response is primed by oral administration and the immune response is boosted by at least one intranasal administration;

the immune response is primed by topical administration and the immune response is boosted by at least one intramuscular administration;

the immune response is primed by topical administration and the immune response is boosted by at least one subcutaneous administration;

the immune response is primed by topical administration and the immune response is boosted by at least one intradermal administration;

the immune response is primed by topical administration and the immune response is boosted by at least one intragastric administration;

the immune response is primed by topical administration and the immune response is boosted by at least one oral administration;

the immune response is primed by topical administration and the immune response is boosted by at least one topical administration;

the immune response is primed by topical administration and the immune response is boosted by at least one intranasal administration.

In one embodiment, the immune response is primed by intranasal administration and the immune response is boosted by at least one intramuscular administration.

In yet another embodiment, the immune response is primed by intranasal administration and the immune response is boosted by at least one intranasal administration.

In yet another embodiment, the immune response is primed by intramuscular administration and the immune response is boosted by at least one intramuscular administration.

In a further aspect, the present invention relates to a vaccine composition comprising a poxviral vector for priming an immune response as defined above or a vaccine combination comprising a poxviral vector and an agent selected from the group consisting of (i) a vector comprising a nucleic acid sequence encoding at least a second antigenic protein or antigenic fragment thereof, (ii) a second antigenic protein or antigenic fragment thereof and (iii) viral like particles.

The term "composition" refers to the combination comprising an antigenic protein or fragment thereof or a viral-like particle or vector comprising a nucleic acid construct and at least one further compound selected from the group consisting of pharmaceutically acceptable carriers, pharmaceutical excipients and adjuvants.

"Pharmaceutically acceptable" means approved by a regulatory agency of the Federal or a state government or listed in the U.S. Pharmacopeia or other generally recognized pharmacopoeia for use in animals, and more particularly in humans.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is one preferred carrier when the pharmaceutical composition is administered intravenously or intranasally by a nebulizer.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Examples of suitable pharmaceutical carriers are described in "Remington's Pharmaceutical Sciences" by E. W. Martin.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

Two groups of 4 macaques were primed with ChAd3IiNS and 50 weeks later boosted with MVA-NS (grey bars) or with MVA-IiNS (black bars). Panel A shows the response by IFNγ ELIspot one week (peak boost) or 3 months post boost (memory). Numbers on y axis represent spot forming cells (SFC)/million PBMC. Panel B shows higher CD8 frequency by IFNγ ICS one week post boost with MVAIiNS (black bars). Numbers on y axis represent % of antigen-specific CD8 T cells producing IFNγ.

Figure 4:
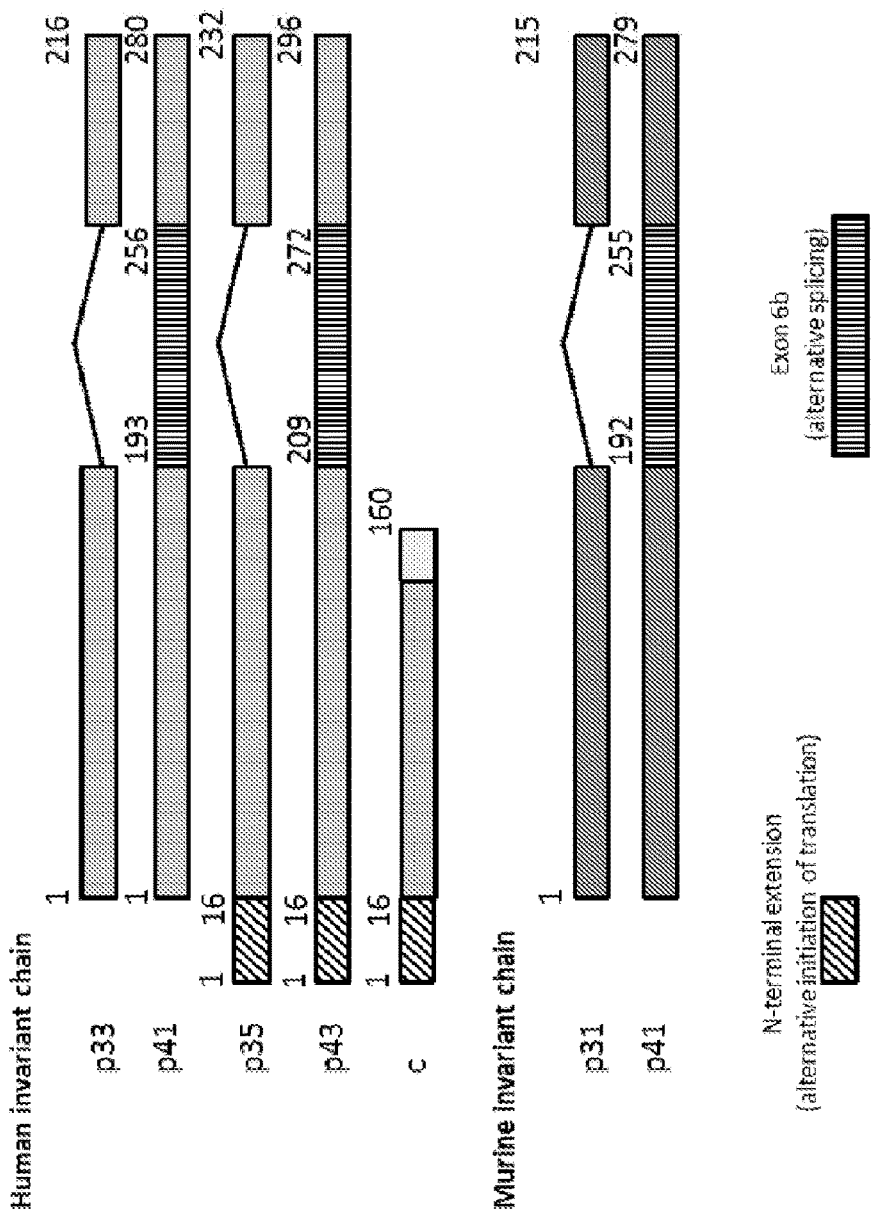

FIG. 4: Schematic diagram showing the four isoforms of human invariant chain (p33, p35, p41, p43, isoform c) and the two isoforms of murine invariant chain (p31, p41). In human p35 and p43 an additional 16 residues are present at the N-terminus due to alternative initiation of translation. In human p41 and p43 isoforms and the murine p41 isoform an additional domain is present due to alternative splicing. The human c isoform lacks two exons relative to human p33 and p35 (three exons relative to human p41 and p43) leading to a frame-shift.

EXAMPLES

Figure 1:
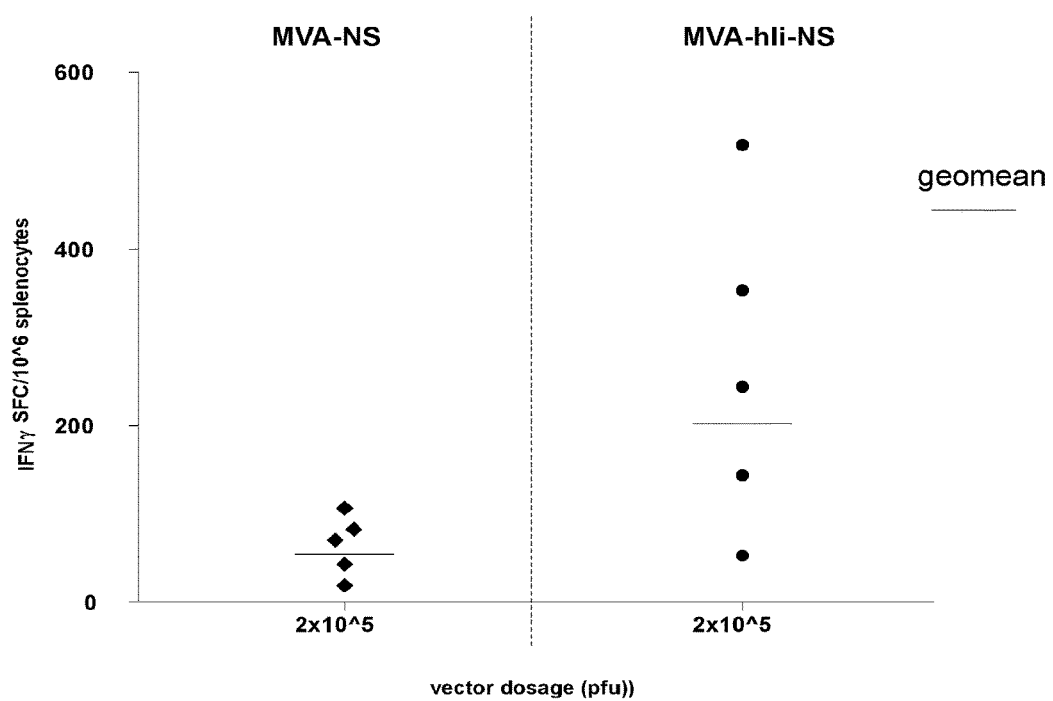
FIG. 1: MVA encoding Invariant chain (Ii)-NS antigen induces stronger T cell response in mice. Two groups of mice were immunized with 2×10^5 plaque forming units (pfu) of MVA comprising NS-antigen (left panel) and with MVA comprising NS linked to invariant chain (right panel). Total T cell response to NS antigen was measured by IFNγ ELISpot and numbers on y axis represent spot forming cells (SFC)/million splenocytes.

Example 1: Priming with MVA Comprising NS Linked to Invariant Chain (MVA-Hli NS) Augments the Generation of HCV-NS Specific T Cells in Mice Two groups of Balb/c mice were immunized intramuscularly with 2×10^5 pfu (plaque forming units) of MVA encoding NS or with the same dose of MVA comprising NS linked to human invariant chain. The NS region encompasses about two thirds of the HCV genome and encodes for five different proteins (NS3, NS4A, NS4B, NS5A and NS5B) that result from the proteolytic cleavage of the HCV polyprotein by the encoded NS3 protease. Ten days after immunization, splenocytes were collected and HCV-NS specific T cell response was evaluated by IFNγ ELIspot using pools of peptides spanning NS. The response was evaluated by summing up reactivities against the six individual peptide pools and subtracting background (spots counted in control wells with no peptide). The level of specific T cells targeting NS was higher in mice primed with the Ii-based MVA vaccine (FIG. 1).

Figure 2:
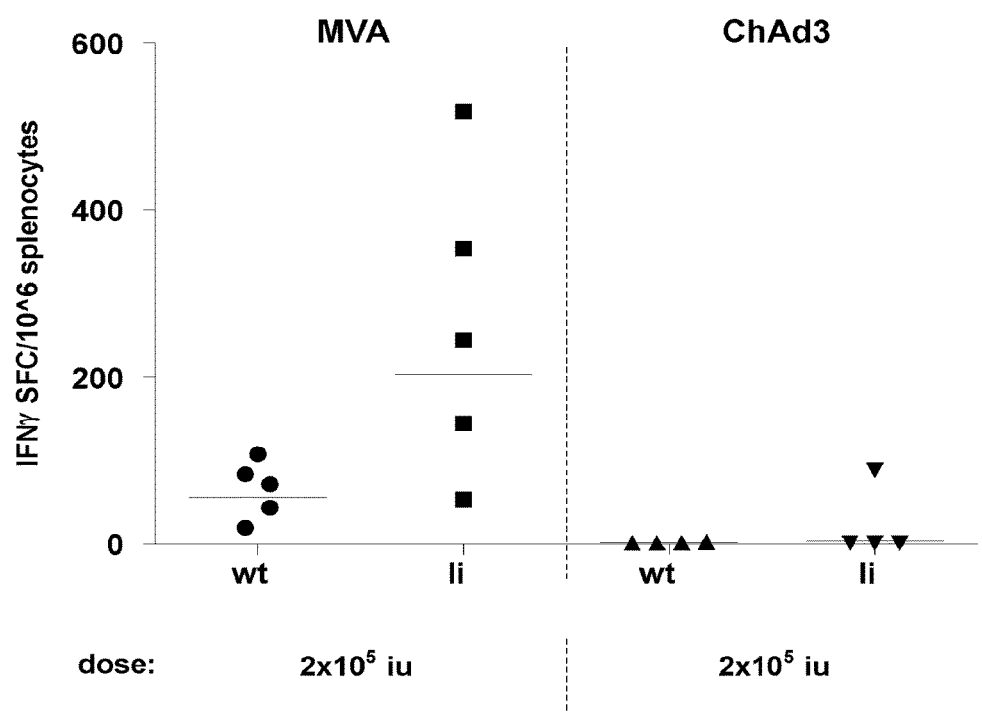
FIG. 2: MVA encoding Invariant chain (Ii)-NS antigen induces stronger T cell response than the corresponding Adeno in mice. Two groups of mice were immunized with MVA encoding NS (MVA wt) or NS linked to human invariant chain (MVAIi). Two additional groups of mice were immunized with a comparable dose of ChAd3 encoding NS (ChAd3 wt) or NS linked to human invariant chain (ChAd3Ii). Total T cell response to NS antigen was measured by IFNγ ELISpot and numbers on y axis represent spot forming cells (SFC)/million splenocytes.

Example 2: Priming with MVA Comprising NS Linked to Invariant Chain (MVA-Hli NS) Induces Stronger T Cell Response in Mice than the Corresponding Adenoviral Vector Two groups of Balb/c mice were immunized intramuscularly with 2×10^5 pfu of MVA encoding NS or with the same dose of MVA comprising NS linked to human invariant chain. Two additional groups of mice were immunized with 2×10^5 iu (infective units) of ChAd3 encoding NS or with the same dose of ChAd3 comprising NS linked to human invariant chain. Peak immune response was evaluated on splenocytes collected 10 and 21 days after immunization with MVA and ChAd3 vectored vaccines, respectively. T cell response was evaluated by IFNγ ELIspot using pools of peptides spanning NS. The results (FIG. 2) show that the Ii-based MVA vaccine induces higher response than the corresponding Ii-based ChAd3 vaccine.

Figure 3:
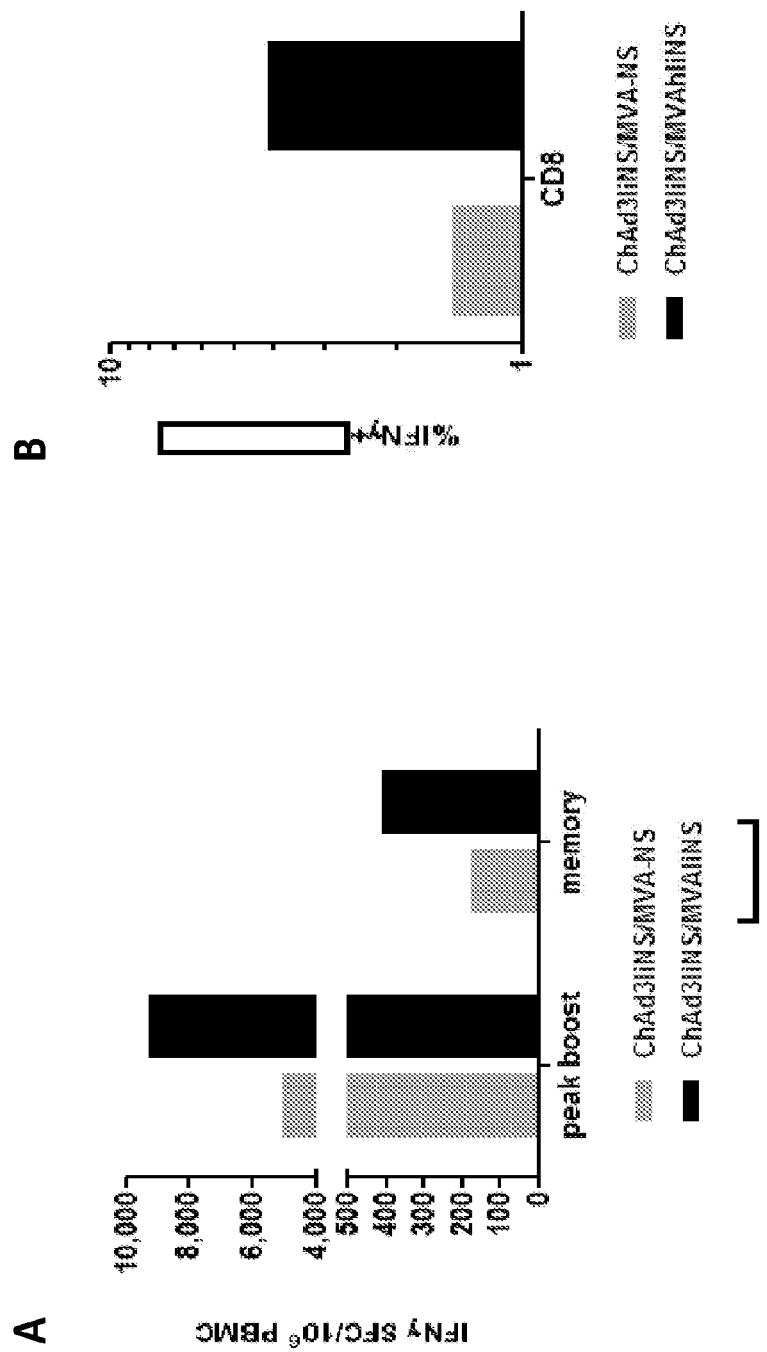
FIG. 3: Boosting with MVA comprising NS linked to invariant chain augments the generation of HCV-NS specific T cells in macaques.

Example 3: Boosting with MVA Comprising NS Linked to Invariant Chain (MVA-Hli NS) Augments the Generation of HCV-NS Specific T Cells in Macaques Two groups of 4 macaques were primed with ChAd3IiNS and 50 weeks later boosted with MVA-NS (grey bars) or with MVA-IiNS (black bars). The injected dose was 1×10$^{10}$ vp for adenoviral vectors, and 2×10$^8$ pfu for MVA vectors. Immune response was evaluated on PBMC collected 1 week (peak response) and 3 months (memory response) after priming by IFNγ ELIspot and IFNγ Intracellular staining (ICS) using pools of peptides spanning NS. As shown in FIG. 3, higher ELISpot response was induced in the group receiving MVAIiNS at both time points (black bars). Panel A shows the response by IFNγ ELIspot one week or 3 months post boost. Panel B shows higher frequency of CD8 T cells producing IFNγ by ICS one week post boost with MVAIiNS (black bars).

Materials and Methods
Adenoviral and MVA Vectors

The ChAd3 vector expressing the entire HCV NS3-5B (NS) region from genotype 1b, strain bk, has been described previously (Colloca et al. *Sci Transl Med* 4(115), 115ra112, 2012). MVA vector expressing the same cassette was derived and prepared as described previously (Cottingham, M. G. et al *PLoS ONE* 3, e1638, 2008; Di Lullo, G. et al. *Virol. Methods* 156, 37-43, 2009). The human Ii (p35, NCBI Reference Sequence: NM_004355) insert was synthetized by GeneArt (Life Technologies, Paisley, UK) and then cloned at the N-terminus of the NS transgene under HCMV and BGHpA control.

Animals and Vaccinations

All experimental procedures were performed in accordance with national and international laws and policies (EEC Council Directive 86/609; Italian Legislative Decree 116/92). The ethical committee of the Italian Ministry of Health approved this research. Animal handling procedures were performed under anesthesia and all efforts were made to minimize suffering and reduce animal numbers. Female 6-week-old Balb/c or C57Bl/6 mice were purchased from Charles River (Como, Italy), and experimental groups of 5 mice each were set. ChAd3 and MVA vectors were administered intramuscularly in the quadriceps by delivering a volume of 50 µl per site (100 µl final volume).

Naïve, female, 11 to 19 years old (weight range 3.2 to 6.5 Kg) Cynomolgus macaques (*macaca fascicularis*) from a purpose bred colony housed at the Institute of Cell Biology and Neurobiology (National Research Council of Italy, Rome), were assigned to experimental groups of four animals each. All immunizations were delivered by intramuscular route in the deltoid muscle injecting 0.5 ml of virus diluted in stabilizing buffer. The injected dose was 1×10$^{10}$ vp for adenoviral vectors, and 2×10$^8$ pfu for MVA vectors. During handling, the animals were anesthetized by i.m. injection of 10 mg/kg ketamine hydrochloride.

Peptides

A set of 494 peptides, 15 amino acids in length, overlapping by 11 amino acids and spanning the open reading frame from NS3-NS5B (1985 a.a.) of HCV genotype 1b strain BK were obtained from BEI Resources (Manassas, Va.).

Ex Vivo IFNγ ELISpot with Mouse and Macaque Samples

MSIP S4510 plates (Millipore) were coated with 10 µg/ml of anti-mouse or anti-monkey IFNγ antibody (both from U-CyTech Utrecht, The Netherlands) overnight at 4° C. After washing and blocking, mouse splenocytes or macaque peripheral blood mononuclear cells (PBMC) were plated in duplicate at two different densities (2×10$^5$ and 4×10$^5$ cells/well) and stimulated overnight with overlapping 15mer peptide pools at a final concentration of 4 µg/ml each single peptide. The peptide diluent DMSO (Sigma-Aldrich, Milan, Italy) and ConA (Sigma-Aldrich, Milan, Italy) were used respectively as negative and positive controls. Plates were developed by subsequent incubations with biotinylated anti-mouse or anti-monkey IFNγ antibody (both from U-CyTech Utrecht, The Netherlands), Streptavidin-Alkaline Phosphatase conjugated (BD Biosciences, NJ) and finally with BCIP/NBT 1-Step solution (Thermo Fisher Scientific, Rockford, Ill.). Plates were acquired and analyzed by an A.EL. VIS automated plate reader. The ELISpot response was considered positive when all of the following conditions were met: IFNγ production present in Con-A stimulated wells; at least 50 specific spots/million splenocytes or PBMC to at least one peptide pool; the number of spots seen in positive wells was three times the number detected in the mock control wells (DMSO); and that responses decreased with cell dilutions. ELISpot data were expressed as IFNγ spot forming cells (SFC) per million splenocytes or PBMC.

Intracellular Cytokine Staining (ICS) and FACS Analysis with Macaque Samples

Briefly, $2\times10^6$ monkey PBMCs were stimulated at 37° C. in 5% $CO_2$ for 15-20 hours using peptide pools as antigen at 2 μg/ml each peptide final concentration in presence of anti-human CD28/CD49d costimulatory antibodies (BD Biosciences, NJ) and Brefeldin A (Sigma-Aldrich, Milan, Italy). DMSO (Sigma-Aldrich, Milan, Italy) was used as negative control, and Staphylococcal enterotoxin B (SEB, Sigma-Aldrich, Milan, Italy) was used as positive control. After overnight stimulation, PBMCs where stained with the following surface antibodies: APC anti-monkey CD3, clone SP34-2; PerCp-Cy5.5 anti-monkey CD4, clone L200; PE anti-human CD8, clone RPA-T8 (all from BD Biosciences, NJ). Intracellular staining was performed after treatment with Cytofix/Cytoperm and in the presence of PermWash (BD Biosciences, NJ) using FITC anti-human IFNγ, clone MD-1 (U-CyTech Utrecht, The Netherlands). Stained cells were acquired on a FACS Canto flow cytometer, and analyzed using DIVA software (BD Biosciences, NJ). At least 30,000 CD8+, CD3+ gated events were acquired for each sample.

The invention claimed is:

1. A method for stimulating an immune response comprising administering to a subject:
    (a) a Modified Vaccinia Ankara vector comprising a nucleic acid construct comprising:
        (i) a nucleic acid sequence encoding at least one antigenic protein or antigenic fragment thereof operatively linked to
        (ii) a nucleic acid encoding at least one invariant chain; and
    (b) an adenoviral vector comprising a nucleic acid sequence encoding at least a second antigenic protein or antigenic fragment thereof;
    wherein the second antigenic protein or antigenic fragment thereof is immunologically identical to the antigenic protein or antigenic fragment thereof encoded by the nucleic acid construct comprised by the Modified Vaccinia Ankara vector.

2. The method of claim 1, wherein the Modified Vaccinia Ankara vector (a) is used for the priming of the immune response and the adenoviral vector of (b) is used for boosting the immune response.

3. The method of claim 1, wherein the adenoviral vector of (b) is used for the priming of the immune response and the Modified Vaccinia Ankara vector (a) is used for boosting the immune response.

4. The method of claim 1, wherein the adenoviral vector is a non-human great ape-derived adenoviral vector.

5. The method of claim 4, wherein the non-human great ape-derived adenoviral vector is a chimpanzee or bonobo adenoviral vector.

6. The method of claim 1, wherein the at least one antigenic protein is a protein of a pathogenic organism, cancer-specific protein, or a protein associated with an abnormal physiological response.

7. The method of claim 6, wherein the pathogenic organism is a virus, a bacterium, a protist or a multicellular parasite.

8. The method of claim 1, wherein the encoded at least one invariant chain is human isoform p33, p35, p41 or p43.

9. The method of claim 1, wherein the encoded at least one invariant chain is a fragment of at least 40 consecutive amino acids of human isoform p33, p35, p41 or p43.

10. The method of claim 1, wherein the encoded at least one invariant chain is murine isoform p31 or p41.

11. The method of claim 1, wherein the encoded at least one invariant chain is a fragment of at least 40 consecutive amino acids of murine isoform p31 or p41.

12. The method of claim 1, wherein the subject is a human.

* * * * *

SEQUENCE LISTING

```
<160> NUMBER OF SEQ ID NOS: 11

<210> SEQ ID NO 1
<211> LENGTH: 232
<212> TYPE: PRT
<213> ORGANISM: Homo sapiens

<400> SEQUENCE: 1

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Glu Ser Leu Glu Leu Glu Asp Pro Ser Ser Gly Leu Gly Val Thr Lys
    210                 215                 220

Gln Asp Leu Gly Pro Val Pro Met
225                 230

<210> SEQ ID NO 2
<211> LENGTH: 699
<212> TYPE: DNA
<213> ORGANISM: Homo sapiens

<400> SEQUENCE: 2
```

-continued

```
atgcacagga ggagaagcag gagctgtcgg gaagatcaga agccagtcat ggatgaccag    60
cgcgacctta tctccaacaa tgagcaactg cccatgctgg ccggcgcccc tggggccccg   120
gagagcaagt gcagccgcgg agccctgtac acaggctttt ccatcctggt gactctgctc   180
ctcgctggcc aggccaccac cgcctacttc ctgtaccagc agcagggccg gctggacaaa   240
ctgacagtca cctcccagaa cctgcagctg gagaacctgc gcatgaagct tcccaagcct   300
cccaagcctg tgagcaagat gcgcatggcc accccgctgc tgatgcaggc gctgcccatg   360
ggagccctgc cccaggggcc catgcagaat gccaccaagt atggcaacat gacagaggac   420
catgtgatgc acctgctcca gaatgctgac cccctgaagg tgtacccgcc actgaagggg   480
agcttcccgg agaacctgag cacccttaag aacaccatgg agaccataga ctggaaggtc   540
tttgagagct ggatgcacca ttggctcctg tttgaaatga gcaggcactc cttggagcaa   600
aagcccactg acgctccacc gaaagagtca ctggaactgg aggacccgtc ttctgggctg   660
ggtgtgacca agcaggatct gggcccagtc cccatgtga                          699
```

<210> SEQ ID NO 3
<211> LENGTH: 215
<212> TYPE: PRT
<213> ORGANISM: Mus

<400> SEQUENCE: 3

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu
    210                 215

<210> SEQ ID NO 4
<211> LENGTH: 648
<212> TYPE: DNA
<213> ORGANISM: Mus

<400> SEQUENCE: 4

```
atggatgacc aacgcgacct catctctaac catgaacagt tgcccatact gggcaaccgc      60
cctagagagc cagaaaggtg cagccgtgga gctctgtaca ccggtgtctc tgtcctggtg     120
gctctgctct tggctgggca ggccaccact gcttacttcc tgtaccagca acagggccgc     180
ctagacaagc tgaccatcac ctcccagaac ctgcaactgg agagccttcg catgaagctt     240
ccgaaatctg ccaaacctgt gagccagatg cggatggcta ctcccttgct gatgcgtcca     300
atgtccatgg ataacatgct ccttgggcct gtgaagaacg ttaccaagta cggcaacatg     360
acccaggacc atgtgatgca tctgctcacg aggtctggac ccctggagta cccgcagctg     420
aaggggacct tcccagagaa tctgaagcat cttaagaact ccatggatgg cgtgaactgg     480
aagatcttcg agagctggat gaagcagtgg ctcttgtttg agatgagcaa gaactccctg     540
gaggagaaga gcccaccga ggctccacct aaagagccac tggacatgga agacctatct     600
tctggcctgg agtgaccag gcaggaactg ggtcaagtca ccctgtga                   648
```

<210> SEQ ID NO 5
<211> LENGTH: 296
<212> TYPE: PRT
<213> ORGANISM: Homo sapiens

<400> SEQUENCE: 5

```
Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
```

```
                245                 250                 255
Gly Thr Glu Val Pro Asn Thr Arg Ser Arg Gly His His Asn Cys Ser
                260                 265                 270

Glu Ser Leu Glu Leu Glu Asp Pro Ser Ser Gly Leu Gly Val Thr Lys
            275                 280                 285

Gln Asp Leu Gly Pro Val Pro Met
        290                 295
```

<210> SEQ ID NO 6
<211> LENGTH: 891
<212> TYPE: DNA
<213> ORGANISM: Homo sapiens

<400> SEQUENCE: 6

```
atgcacagga ggagaagcag gagctgtcgg gaagatcaga agccagtcat ggatgaccag     60
cgcgacctta tctccaacaa tgagcaactg cccatgctgg gccggcgccc tggggccccg    120
gagagcaagt gcagccgcgg agccctgtac acaggctttt ccatcctggt gactctgctc    180
ctcgctggcc aggccaccac cgcctacttc ctgtaccagc agcagggccg gctggacaaa    240
ctgacagtca cctcccagaa cctgcagctg gagaacctgc gcatgaagct tcccaagcct    300
cccaagcctg tgagcaagat gcgcatggcc accccgctgc tgatgcaggc gctgcccatg    360
ggagccctgc cccagggggcc catgcagaat gccaccaagt atggcaacat gacagaggac    420
catgtgatgc acctgctcca gaatgctgac cccctgaagg tgtacccgcc actgaagggg    480
agcttcccgg agaacctgag acaccttaag aacaccatgg agaccataga ctggaaggtc    540
tttgagagct ggatgcacca ttggctcctg tttgaaatga gcaggcactc cttggagcaa    600
aagcccactg acgctccacc gaaagtactg accaagtgcc aggaagaggt cagccacatc    660
cctgctgtcc acccgggttc attcaggccc aagtgcgacg agaacggcaa ctatctgcca    720
ctccagtgct atgggagcat cggctactgc tggtgtgtct tccccaacgg cacggaggtc    780
cccaacacca gaagccgcgg gcaccataac tgcagtgagt cactggaact ggaggacccg    840
tcttctgggc tgggtgtgac caagcaggat ctgggcccag tccccatgtg a             891
```

<210> SEQ ID NO 7
<211> LENGTH: 279
<212> TYPE: PRT
<213> ORGANISM: Mus

<400> SEQUENCE: 7

```
Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
```

```
                    115                 120                 125
Leu Thr Arg Ser Gly Pro Leu Glu Tyr Pro Gln Leu Lys Gly Thr Phe
            130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Val
            180                 185                 190

Leu Thr Lys Cys Gln Glu Glu Val Ser His Ile Pro Ala Val Tyr Pro
        195                 200                 205

Gly Ala Phe Arg Pro Lys Cys Asp Glu Asn Gly Asn Tyr Leu Pro Leu
    210                 215                 220

Gln Cys His Gly Ser Thr Gly Tyr Cys Trp Cys Val Phe Pro Asn Gly
225                 230                 235                 240

Thr Glu Val Pro His Thr Lys Ser Arg Gly Arg His Asn Cys Ser Glu
                245                 250                 255

Pro Leu Asp Met Glu Asp Leu Ser Ser Gly Leu Gly Val Thr Arg Gln
            260                 265                 270

Glu Leu Gly Gln Val Thr Leu
        275

<210> SEQ ID NO 8
<211> LENGTH: 840
<212> TYPE: DNA
<213> ORGANISM: Mus

<400> SEQUENCE: 8
atggatgacc aacgcgacct catctctaac catgaacagt tgcccatact gggcaaccgc      60
cctagagagc cagaaaggtg cagccgtgga gctctgtaca ccggtgtctc tgtcctggtg     120
gctctgctct tggctgggca ggccaccact gcttacttcc tgtaccagca acagggccgc     180
ctagacaagc tgaccatcac ctcccagaac ctgcaactgg agagccttcg catgaagctt     240
ccgaaatctg ccaaacctgt gagccagatg cggatggcta ctcccttgct gatgcgtcca     300
atgtccatgg ataacatgct ccttgggcct gtgaagaacg ttaccaagta cggcaacatg     360
acccaggacc atgtgatgca tctgctcacg aggtctggac ccctggagta cccgcagctg     420
aaggggacct tcccagagaa tctgaagcat cttaagaact ccatggatgg cgtgaactgg     480
aagatcttcg agagctggat gaagcagtgg ctcttgtttg agatgagcaa gaactccctg     540
gaggagaaga gcccaccga ggctccacct aaagtactga ccaagtgcca ggaagaagtc     600
agccacatcc ctgccgtcta cccgggtgcg ttccgtccca gtgcgacga gaacggtaac      660 tatttgccac tccagtgcca cgggagcact ggctactgct ggtgtgtgtt ccccaacggc     720
actgaggttc ctcacaccaa gagccgcggg cgccataact gcagtgagcc actggacatg     780
gaagacctat cttctggcct gggagtgacc aggcaggaac tgggtcaagt cacccctgtga     840

<210> SEQ ID NO 9
<211> LENGTH: 160
<212> TYPE: PRT
<213> ORGANISM: Homo sapiens

<400> SEQUENCE: 9

Met His Arg Arg Arg Ser Arg Ser Cys Arg Glu Asp Gln Lys Pro Val
1               5                   10                  15
```

```
Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
        130                 135                 140

Leu Leu Gln Ser His Trp Asn Trp Arg Thr Arg Leu Leu Gly Trp Val
145                 150                 155                 160

<210> SEQ ID NO 10
<211> LENGTH: 483
<212> TYPE: DNA
<213> ORGANISM: Homo sapiens

<400> SEQUENCE: 10
atgcacagga ggagaagcag gagctgtcgg gaagatcaga agccagtcat ggatgaccag    60
cgcgacctta tctccaacaa tgagcaactg cccatgctgg gccggcgccc tggggccccg   120
gagagcaagt gcagccgcgg agccctgtac acaggctttt ccatcctggt gactctgctc   180
ctcgctggcc aggccaccac cgcctacttc ctgtaccagc agcagggccg gctggacaaa   240
ctgacagtca cctcccagaa cctgcagctg gagaacctgc gcatgaagct tcccaagcct   300
cccaagcctg tgagcaagat gcgcatggcc accccgctgc tgatgcaggc gctgcccatg   360
ggagccctgc cccagggggcc catgcagaat gccaccaagt atggcaacat gacagaggac   420
catgtgatga cctgctcca gagtcactgg aactggagga cccgtcttct gggctgggtg   480
tga                                                                 483

<210> SEQ ID NO 11
<211> LENGTH: 1985
<212> TYPE: PRT
<213> ORGANISM: Artificial Sequence
<220> FEATURE:
<223> OTHER INFORMATION: Met-NS3-NS4A-NS4B-NS5A-NS5B polypeptide

<400> SEQUENCE: 11

Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Lys Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
```

-continued

```
                85                  90                  95
Pro Cys Thr Cys Gly Ser Ser Asp Leu Tyr Leu Val Thr Arg His Ala
                100                 105                 110
Asp Val Ile Pro Val Arg Arg Gly Asp Ser Arg Gly Ser Leu Leu
                115                 120                 125
Ser Pro Arg Pro Val Ser Tyr Leu Lys Gly Ser Ser Gly Gly Pro Leu
130                 135                 140
Leu Cys Pro Ser Gly His Ala Val Gly Ile Phe Arg Ala Ala Val Cys
145                 150                 155                 160
Thr Arg Gly Val Ala Lys Ala Val Asp Phe Val Pro Val Glu Ser Met
                165                 170                 175
Glu Thr Thr Met Arg Ser Pro Val Phe Thr Asp Asn Ser Ser Pro Pro
                180                 185                 190
Ala Val Pro Gln Ser Phe Gln Val Ala His Leu His Ala Pro Thr Gly
                195                 200                 205
Ser Gly Lys Ser Thr Lys Val Pro Ala Ala Tyr Ala Ala Gln Gly Tyr
                210                 215                 220
Lys Val Leu Val Leu Asn Pro Ser Val Ala Ala Thr Leu Gly Phe Gly
225                 230                 235                 240
Ala Tyr Met Ser Lys Ala His Gly Ile Asp Pro Asn Ile Arg Thr Gly
                245                 250                 255
Val Arg Thr Ile Thr Thr Gly Ala Pro Val Thr Tyr Ser Thr Tyr Gly
                260                 265                 270
Lys Phe Leu Ala Asp Gly Gly Cys Ser Gly Gly Ala Tyr Asp Ile Ile
                275                 280                 285
Ile Cys Asp Glu Cys His Ser Thr Asp Ser Thr Thr Ile Leu Gly Ile
                290                 295                 300
Gly Thr Val Leu Asp Gln Ala Glu Thr Ala Gly Ala Arg Leu Val Val
305                 310                 315                 320
Leu Ala Thr Ala Thr Pro Pro Gly Ser Val Thr Val Pro His Pro Asn
                325                 330                 335
Ile Glu Glu Val Ala Leu Ser Asn Thr Gly Glu Ile Pro Phe Tyr Gly
                340                 345                 350
Lys Ala Ile Pro Ile Glu Ala Ile Arg Gly Gly Arg His Leu Ile Phe
                355                 360                 365
Cys His Ser Lys Lys Lys Cys Asp Glu Leu Ala Ala Lys Leu Ser Gly
                370                 375                 380
Leu Gly Ile Asn Ala Val Ala Tyr Tyr Arg Gly Leu Asp Val Ser Val
385                 390                 395                 400
Ile Pro Thr Ile Gly Asp Val Val Val Ala Thr Asp Ala Leu Met
                405                 410                 415
Thr Gly Tyr Thr Gly Asp Phe Asp Ser Val Ile Asp Cys Asn Thr Cys
                420                 425                 430
Val Thr Gln Thr Val Asp Phe Ser Leu Asp Pro Thr Phe Thr Ile Glu
                435                 440                 445
Thr Thr Thr Val Pro Gln Asp Ala Val Ser Arg Ser Gln Arg Arg Gly
                450                 455                 460
Arg Thr Gly Arg Gly Arg Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Ser Val
                500                 505                 510
```

```
Arg Leu Arg Ala Tyr Leu Asn Thr Pro Gly Leu Pro Val Cys Gln Asp
    515                 520                 525

His Leu Glu Phe Trp Glu Ser Val Phe Thr Gly Leu Thr His Ile Asp
530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
    595                 600                 605

Glu Val Thr Leu Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Arg Pro Ala Ile Val Pro Asp
            660                 665                 670

Arg Glu Phe Leu Tyr Gln Glu Phe Asp Glu Met Glu Glu Cys Ala Ser
    675                 680                 685

His Leu Pro Tyr Ile Glu Gln Gly Met Gln Leu Ala Glu Gln Phe Lys
    690                 695                 700

Gln Lys Ala Leu Gly Leu Leu Gln Thr Ala Thr Lys Gln Ala Glu Ala
705                 710                 715                 720

Ala Ala Pro Val Val Glu Ser Lys Trp Arg Ala Leu Glu Thr Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
    755                 760                 765

Thr Ala Ser Ile Thr Ser Pro Leu Thr Thr Gln Ser Thr Leu Leu Phe
    770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
    835                 840                 845

Pro Ser Thr Glu Asp Leu Val Asn Leu Leu Pro Ala Ile Leu Ser Pro
    850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
                885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Ser Leu Thr Ile
    915                 920                 925
```

-continued

```
Thr Gln Leu Leu Lys Arg Leu His Gln Trp Ile Asn Glu Asp Cys Ser
            930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Gln Leu Pro Gly Val Pro Phe Phe Ser Cys Gln Arg Gly Tyr Lys Gly
            980                 985                 990
Val Trp Arg Gly Asp Gly Ile Met Gln Thr Thr Cys Pro Cys Gly Ala
            995                1000                1005
Gln Ile Thr Gly His Val Lys Asn Gly Ser Met Arg Ile Val Gly Pro
       1010                1015                1020
Lys Thr Cys Ser Asn Thr Trp His Gly Thr Phe Pro Ile Asn Ala Tyr
1025                1030                1035                1040
Thr Thr Gly Pro Cys Thr Pro Ser Pro Ala Pro Asn Tyr Ser Arg Ala
                1045                1050                1055
Leu Trp Arg Val Ala Ala Glu Glu Tyr Val Glu Val Thr Arg Val Gly
            1060                1065                1070
Asp Phe His Tyr Val Thr Gly Met Thr Thr Asp Asn Val Lys Cys Pro
            1075                1080                1085
Cys Gln Val Pro Ala Pro Glu Phe Phe Thr Glu Val Asp Gly Val Arg
       1090                1095                1100
Leu His Arg Tyr Ala Pro Ala Cys Arg Pro Leu Leu Arg Glu Glu Val
1105                1110                1115                1120
Thr Phe Gln Val Gly Leu Asn Gln Tyr Leu Val Gly Ser Gln Leu Pro
                1125                1130                1135
Cys Glu Pro Glu Pro Asp Val Ala Val Leu Thr Ser Met Leu Thr Asp
            1140                1145                1150
Pro Ser His Ile Thr Ala Glu Thr Ala Lys Arg Arg Leu Ala Arg Gly
            1155                1160                1165
Ser Pro Pro Ser Leu Ala Ser Ser Ser Ala Ser Gln Leu Ser Ala Pro
       1170                1175                1180
Ser Leu Lys Ala Thr Cys Thr Thr His His Val Ser Pro Asp Ala Asp
1185                1190                1195                1200
Leu Ile Glu Ala Asn Leu Leu Trp Arg Gln Glu Met Gly Gly Asn Ile
                1205                1210                1215
Thr Arg Val Glu Ser Glu Asn Lys Val Val Leu Asp Ser Phe Asp
            1220                1225                1230
Pro Leu Arg Ala Glu Glu Asp Glu Arg Glu Val Ser Val Pro Ala Glu
            1235                1240                1245
Ile Leu Arg Lys Ser Lys Lys Phe Pro Ala Ala Met Pro Ile Trp Ala
       1250                1255                1260
Arg Pro Asp Tyr Asn Pro Pro Leu Leu Glu Ser Trp Lys Asp Pro Asp
1265                1270                1275                1280
Tyr Val Pro Pro Val Val His Gly Cys Pro Leu Pro Pro Ile Lys Ala
                1285                1290                1295
Pro Pro Ile Pro Pro Pro Arg Arg Lys Arg Thr Val Val Leu Thr Glu
            1300                1305                1310
Ser Ser Val Ser Ser Ala Leu Ala Glu Leu Ala Thr Lys Thr Phe Gly
            1315                1320                1325
Ser Ser Glu Ser Ser Ala Val Asp Ser Gly Thr Ala Thr Ala Leu Pro
       1330                1335                1340
Asp Gln Ala Ser Asp Asp Gly Asp Lys Gly Ser Asp Val Glu Ser Tyr
```

```
              1345                1350                1355                1360
Ser Ser Met Pro Pro Leu Glu Gly Glu Pro Gly Asp Pro Asp Leu Ser
                1365                1370                1375
Asp Gly Ser Trp Ser Thr Val Ser Glu Glu Ala Ser Glu Asp Val Val
                1380                1385                1390
Cys Cys Ser Met Ser Tyr Thr Trp Thr Gly Ala Leu Ile Thr Pro Cys
                1395                1400                1405
Ala Ala Glu Glu Ser Lys Leu Pro Ile Asn Ala Leu Ser Asn Ser Leu
                1410                1415                1420
Leu Arg His His Asn Met Val Tyr Ala Thr Thr Ser Arg Ser Ala Gly
1425                1430                1435                1440
Leu Arg Gln Lys Lys Val Thr Phe Asp Arg Leu Gln Val Leu Asp Asp
                1445                1450                1455
His Tyr Arg Asp Val Leu Lys Glu Met Lys Ala Lys Ala Ser Thr Val
                1460                1465                1470
Lys Ala Lys Leu Leu Ser Val Glu Glu Ala Cys Lys Leu Thr Pro Pro
                1475                1480                1485
His Ser Ala Lys Ser Lys Phe Gly Tyr Gly Ala Lys Asp Val Arg Asn
                1490                1495                1500
Leu Ser Ser Lys Ala Val Asn His Ile His Ser Val Trp Lys Asp Leu
1505                1510                1515                1520
Leu Glu Asp Thr Val Thr Pro Ile Asp Thr Thr Ile Met Ala Lys Asn
                1525                1530                1535
Glu Val Phe Cys Val Gln Pro Glu Lys Gly Gly Arg Lys Pro Ala Arg
                1540                1545                1550
Leu Ile Val Phe Pro Asp Leu Gly Val Arg Val Cys Glu Lys Met Ala
                1555                1560                1565
Leu Tyr Asp Val Val Ser Thr Leu Pro Gln Val Val Met Gly Ser Ser
                1570                1575                1580
Tyr Gly Phe Gln Tyr Ser Pro Gly Gln Arg Val Glu Phe Leu Val Asn
1585                1590                1595                1600
Thr Trp Lys Ser Lys Lys Asn Pro Met Gly Phe Ser Tyr Asp Thr Arg
                1605                1610                1615
Cys Phe Asp Ser Thr Val Thr Glu Asn Asp Ile Arg Val Glu Glu Ser
                1620                1625                1630
Ile Tyr Gln Cys Cys Asp Leu Ala Pro Glu Ala Arg Gln Ala Ile Lys
                1635                1640                1645
Ser Leu Thr Glu Arg Leu Tyr Ile Gly Gly Pro Leu Thr Asn Ser Lys
                1650                1655                1660
Gly Gln Asn Cys Gly Tyr Arg Arg Cys Arg Ala Ser Gly Val Leu Thr
1665                1670                1675                1680
Thr Ser Cys Gly Asn Thr Leu Thr Cys Tyr Leu Lys Ala Ser Ala Ala
                1685                1690                1695
Cys Arg Ala Ala Lys Leu Gln Asp Cys Thr Met Leu Val Asn Ala Ala
                1700                1705                1710
Gly Leu Val Val Ile Cys Glu Ser Ala Gly Thr Gln Glu Asp Ala Ala
                1715                1720                1725
Ser Leu Arg Val Phe Thr Glu Ala Met Thr Arg Tyr Ser Ala Pro Pro
                1730                1735                1740
Gly Asp Pro Pro Gln Pro Glu Tyr Asp Leu Glu Leu Ile Thr Ser Cys
1745                1750                1755                1760
Ser Ser Asn Val Ser Val Ala His Asp Ala Ser Gly Lys Arg Val Tyr
                1765                1770                1775
```

```
Tyr Leu Thr Arg Asp Pro Thr Thr Pro Leu Ala Arg Ala Ala Trp Glu
            1780            1785            1790

Thr Ala Arg His Thr Pro Val Asn Ser Trp Leu Gly Asn Ile Ile Met
        1795            1800            1805

Tyr Ala Pro Thr Leu Trp Ala Arg Met Ile Leu Met Thr His Phe Phe
    1810            1815            1820

Ser Ile Leu Leu Ala Gln Glu Gln Leu Glu Lys Ala Leu Asp Cys Gln
1825            1830            1835            1840

Ile Tyr Gly Ala Cys Tyr Ser Ile Glu Pro Leu Asp Leu Pro Gln Ile
                1845            1850            1855

Ile Glu Arg Leu His Gly Leu Ser Ala Phe Ser Leu His Ser Tyr Ser
            1860            1865            1870

Pro Gly Glu Ile Asn Arg Val Ala Ser Cys Leu Arg Lys Leu Gly Val
        1875            1880            1885

Pro Pro Leu Arg Val Trp Arg His Arg Ala Arg Ser Val Arg Ala Arg
    1890            1895            1900

Leu Leu Ser Gln Gly Gly Arg Ala Ala Thr Cys Gly Lys Tyr Leu Phe
1905            1910            1915            1920

Asn Trp Ala Val Lys Thr Lys Leu Lys Leu Thr Pro Ile Pro Ala Ala
                1925            1930            1935

Ser Gln Leu Asp Leu Ser Gly Trp Phe Val Ala Gly Tyr Ser Gly Gly
            1940            1945            1950

Asp Ile Tyr His Ser Leu Ser Arg Ala Arg Pro Arg Trp Phe Met Leu
        1955            1960            1965

Cys Leu Leu Leu Ser Val Gly Val Gly Ile Tyr Leu Leu Pro Asn
    1970            1975            1980

Arg
1985
```